United States Patent [19]
Haunsø et al.

[11] Patent Number: 5,939,270
[45] Date of Patent: Aug. 17, 1999

[54] MARKERS FOR ORGAN REJECTION

[75] Inventors: Stig Haunsø, Rungsted; Jørn Carlsen, Charlottenlund; Keld Kjeldsen, København Ø; Thais Taaning Johansen, Skodsborg; Peter Mose Larsen, Aarhus C; Ulla Andrup Jensen, Galten; Stephen John Fey, Aarhus C, all of Denmark; Marc Boutry, Brussels; Hervé Degand, Havre-Mons, both of Belgium

[73] Assignee: Universite Catholique de Louvain, Louvain La Neuve, Belgium

[21] Appl. No.: 08/424,292

[22] PCT Filed: Dec. 23, 1994

[86] PCT No.: PCT/EP94/04295

§ 371 Date: Apr. 18, 1995

§ 102(e) Date: Apr. 18, 1995

[87] PCT Pub. No.: WO95/17425

PCT Pub. Date: Jun. 29, 1995

[30] Foreign Application Priority Data

Dec. 23, 1993 [DK] Denmark ................................. 1453/93

[51] Int. Cl.$^6$ ............................. C12Q 1/00; G01N 33/50
[52] U.S. Cl. .............................. 435/7.1; 435/4; 435/7.21; 435/7.92; 435/29; 435/810; 435/975; 436/86; 436/518; 436/536; 530/350; 530/841
[58] Field of Search ................................. 435/4, 29, 7.1, 435/7.21, 7.92, 810, 975; 436/86, 518, 536; 530/350, 841

[56] References Cited

U.S. PATENT DOCUMENTS

| Re. 35,419 | 1/1997 | Kilty et al. ................................ 435/7.4 |
| 4,434,234 | 2/1984 | Adams et al. ............................ 436/86 |
| 5,217,868 | 6/1993 | Kilty et al. ................................ 435/7.4 |
| 5,223,396 | 6/1993 | Rothlein et al. ........................ 435/7.21 |
| 5,225,329 | 7/1993 | Marks ....................................... 435/7.9 |
| 5,364,793 | 11/1994 | Cameron, Sr. et al. .................. 436/86 |
| 5,484,707 | 1/1996 | Goldblum et al. ..................... 435/7.92 |
| 5,527,884 | 6/1996 | Russell et al. ........................... 530/350 |

FOREIGN PATENT DOCUMENTS

| 0336155 | 10/1989 | European Pat. Off. . |
| 2268935 | 1/1994 | United Kingdom . |
| WO 93/03381 | 2/1993 | WIPO . |

OTHER PUBLICATIONS

Amersham Life Science Products Catalogue 1992, pp. 54–56, 66, 132.

Pearlstone et al. (1986) J. Biol. Chem. 261:16795–810.

*Primary Examiner*—David Saunders
*Attorney, Agent, or Firm*—Klauber & Jackson

[57] ABSTRACT

Provided herein are human proteins or xenogeneic homologs thereof, which are predictive markers for acute allograft rejection, processes for obtaining the proteins of the invention, nucleotide sequences which encode the proteins, and antibodies to the proteins. Also provided are methods of assaying biological samples for the presence, and optionally the amounts of proteins of the invention, a kit for assaying such proteins in a bodily sample, and a method and kit related to diagnosis and prognosis of organ rejection in a subject.

16 Claims, 3 Drawing Sheets

MARKERS FOR ORGAN REJECTION

FIELD OF THE INVENTION

The present invention relates to the diagnosis and prognosis of organ rejection in a subject. More particularly, the invention relates to allograft rejection, e.g., heart transplant rejection. The invention provides immunological, biochemical, and molecular biological detection methods, and kits for use by medical practitioners for detecting rejection phenomena.

This invention particularly concerns human proteins which are predictive markers for acute allograft rejection, processes for obtaining said proteins, DNA and RNA coding for said proteins, methods of assaying biological samples from human beings for the presence, and optionally the amounts, of said proteins, an assay kit for use in said methods, polyclonal and monoclonal antibodies against each of said proteins, a method of predicting acute rejection in a human patient having undergone organ transplantation, or suffering from an autoimmune disease, inflammatory disease, or ischemic injury, and associated methods for the diagnosis of inflammation or diseases in various organ systems of the human body.

BACKGROUND OF THE INVENTION

Since its inception in 1968, heart transplantation has developed into a therapeutic possibility for patients with end-stage cardiac failure. More than 230 transplantation centers have been established throughout the world, and more than 25,000 patients world-wide have undergone heart transplantation (Kaye, 1993, J. Heart Lung Transplant. 12:541–548). Initially, the major drawback following transplantation was the risk of rejection due to the recipient's own immune system. Although the introduction of immunosuppressive agents, notably cyclosporin, has improved the situation, rejection still remains an important challenge for the treatment of transplantation patients (Oyer et al., 1991, Transplant. Proc. 15(Suppl. 1):2546–2552; Burdick and Kittur, 1991, Transplant. Proc. 23:2047–2051).

Acute rejection remains the major cause of morbidity and mortality following human heart transplantation, and is a severe complication or cause of death in other organ transplantation procedures as well. Two major analytical methods are used to evaluate the state of the transplanted heart (Carrier, 1991). The first method involves evaluation of the induction and expression of immunity against the allograft, for example cytoimmunological monitoring of lymphocytes, and analysis of cellular markers (such as soluble CD-4, CD-8, IL-2 receptor, and T cell antigen receptor), cytokines, and lymphokines associated with lymphocyte activation. The second method involves evaluation of the graft function and status, e.g., by echo doppler, radiologic imaging, and magnetic resonance imaging. The first grading system of acute cellular rejection was introduced in 1973 (Caves et al., 1973, Thorac. Cardiovasc. Surg. 66:461–466). A grading system which currently is in general use is based on the degree of infiltration and myocyte necrosis in endomyocardial biopsies and uses the grades 0, 1A, 1B, 2, 3A, 3B and 4 (Billingham et al., 1990, J. Heart Transplant. 9:588–593). While there is considerable disagreement as to which methods are the most accurate prognosticators of heart status after transplantation, it is commonly agreed that all of the approaches used in the art inadequately predict all, or even a satisfactory number of, cases of acute rejection early enough (Billingham, 1990, Prog. Cardiovasc. Dis. 33:11–18; Carrier, 1991, Can. J. Surg. 34:569–572; and Burdick and Kittur, 1991, Transplant. Proc. 23:2047–2051). In particular, the amount of lymphocytic infiltrate detected pathologically may not be helpful in diagnosing rejection episodes and determining the need for treatment (Auchincloss and Sachs, 1993, "Transplantation Graft Rejection," in *Fundamental Immunology, Third Edition*, William E. Paul editor, Raven Press: New York, pp. 1099–1141, 1129). Similarly, the level of soluble IL-2 receptors, while indicative of immune activation, is associated closely with viral infection as well as organ rejection. Since viral infection represents one of the common differential diagnoses at the time of transplant organ dysfunction, such nonspecific assays for immunologic function suffer from an inability to determine the target of immune activation (Auchincloss and Sachs, supra, p. 1129).

Recently, Ferran et al. (1993, Transplantation 55:605–609) analyzed the expression of the cell adhesion molecules ELAM-1, VCAM-1, and ICAM-1 on myocardial biopsy specimens from 16 cardiac allograft recipients either for routine monitoring or for the investigation of suspected rejection. Three to six sequential biopsies taken at one-week intervals were analyzed by means of conventional histology and immunohistochemistry (Ferraln et al., supra). They found that the biopsies of 7 patients who did not develop rejection during the study were negative for VCAM-1 and ELAM-1, although faint ICAM-1 staining was present on capillaries, reflecting constitutive expression. In 3 patients with clear-cut clinical and histological signs of acute rejection, intense VCAM-1 and ICAM-1 expression was detected, but ELAM-1 was undetectable in all three cases. In four out of 6 patients who developed acute rejection during the course of the study ELAM-1 and VCAM-1 were expressed one or two weeks before the histological diagnosis of rejection, and only VCAM-1 expression was observed in the other two. Also, in the four patients, ELAM-1 expression was short lived and had disappeared by the time CD3 cellular infiltrate was detected, thus extending in vivo the finding that ELAM-1 expression is usually transient in vitro. Based on these results, the authors suggested that both ELAM-1 and VCAM-1 expression may have a predictive value in acute cardiac allograft rejection, adding that since ELAM-1 expression is transient, careful monitoring with a close sampling interval would be necessary.

ICAM-1 is a marker of immune activation and endothelial damage, but has not been found to be correlated with cellular rejection as assessed by endomyocardial biopsy (Ballantyne et al., 1994, J. Heart Lung Transplant. 13:597–603). Markers of myocardial damage such as creatine kinase MB and myoglobin have not been useful in identifying rejection in heart transplanted patients (Ladowski et al., 1992, Chest 102:1520–1; Jennison et al., 1992, Circulation Suppl 86:1–844; Gash et al., 1994, J. Heart Lung Transplant. 13:451–454).

Patients often go through unpredictable phases of varying degree of rejection.

Early diagnosis of the approach of rejection is essential to keep the patient in a state of stable non-rejection and avoiding advanced states of tissue destruction, while keeping the level of immunosuppressive therapy as low as possible to avoid onset of opportunistic infections.

Rejection phenomena are not limited to heart allografts. All organ transplants are subject to rejection (host versus graft disease). In addition, rejection-like events accompany graft versus host disease (where transplanted leukocytes and lymphocytes attack the host tissues) and autoimmune disease (e.g., rheumatic fever, in which the heart is the target of an autoantibodies and auto-reactive lymphocytes). In all cases, while aggressive immunosuppression is indicated to reverse or correct the immune reaction, the associated danger of facilitation of opportunistic infections constrains the use of immunosuppression.

Accordingly, there is a need in the art for a highly accurate prognostic indicator of the likelihood of onset of organ rejection. There is a further need in the art for a diagnostic indicator of the grade of cellular rejection (as in Billingham et al., supra).

There is a further need in the art for identification and detection of a specific and sensitive marker of organ rejection to direct administration of immunosuppressive agents, thus avoiding the need to maintain constant immunosuppression in a subject, and allowing for aggressive immunosuppressive therapy to head-off a rejection episode.

The citation of any reference herein should not be construed as an admission that such reference is prior art to the instant invention.

SUMMARY OF THE INVENTION

In its primary aspect, the present invention is directed to a method for evaluating the likelihood of organ rejection comprising detecting the presence of an amount of a marker indicative of organ rejection in a biological sample from a subject suspected of being in danger of organ rejection, wherein the marker is a protein expressed by the cells in the organ suspected of being rejected, and wherein detection of the presence of an amount of the marker is indicative of an increased likelihood of or the onset of organ rejection. Preferably, the method comprises detecting the presence of an amount of more than one marker indicative of organ rejection in a biological sample from a subject suspected of being in danger of organ rejection. An amount of a marker or markers indicative of organ rejection is an statistically significant increased amount compared to the amount (or level) present in a normal organ, or in a transplanted organ prior to initiation of rejection.

The levels of the markers of the present invention increase dramatically prior to or concomitant with a rejection episode. In a preferred embodiment, the markers of the invention have a much more dramatic increase in relative expression than VCAM-1. In a specific aspect, the level of expression of a marker of the invention is increased at least three-fold, preferably at least 10-fold, more preferably at least 20-fold, and most preferably at least 50 fold relative to normal tissues. In specific embodiments exemplified herein, an increase in the level of expression of greater than 100-fold is observed. Moreover, some of the markers are sufficiently sensitive to provide for detection of an impending rejection episode at least four weeks prior to its onset. The markers of the invention are not considered to stem from the activation of an infection because they are found in cardiac tissue immediately prior to implantation if very low, but definite amounts and thus appear to be cellular proteins of the heart. In particular, the markers of the invention may not be proteins from unstimulated lymphocytes or leukocytes, which proteins include but not limited to the cytokines tumor necrosis factor-α, lymphotoxin (TNF-β), the interleukins, the interferons, or soluble forms of lymphocyte-associated integral membrane proteins (e.g., soluble CD-4, soluble CD-8, soluble IL-2 receptor, soluble T cell antigen receptor, and the like).

Moreover, since a subject believed to be in danger of organ rejection receives immunosuppressive therapy, it is likely that the levels of these lymphocyte and leukocyte proteins will be suppressed, rather than increased.

The present invention advantageously provides for diagnosis of an impending rejection episode as early as four weeks prior to onset, i.e., at least four weeks earlier than conventional diagnosis. Thus, the markers of the invention are highly sensitive prognostic indicators of the course and extent of organ viability and rejection.

In a specific embodiment, the invention provides for detecting rejection of the heart. In a more specific embodiment, the heart is an allograft transplant.

Thus, the present invention concerns a protein selected from the group consisting of human proteins which are predictive markers for acute rejection and exhibit the following characteristics by two dimensional (2D) gel electrophoresis of endomyocardial biopsies in IEF and NEPHGE gels, respectively, and a 12.5% polyacrylamide gel, as disclosed herein:

| Protein | pI | MW |
|---|---|---|
| IEF 1A | 5.92 | 122,600 |
| IEF 1B | 5.83 | 123,100 |
| IEF 2A | 6.20 | 75,500 |
| IEF 2B | 6.15 | 76,100 |
| IEF 3 | 6.09 | 49,900 |
| IEF 4 | 6.86 | 42,700 |
| IEF 5A | 6.12 | 39,100 |
| IEF 5B | 6.08 | 39,200 |
| IEF 5C | 5.96 | 39,300 |
| IEF 6 | 5.07 | 21,800 |
| IEF 7 | 5.60 | 20,400 |
| IEF 8 | 5.72 | 16,400 |
| NEPHGE 1A | 7.92 | 78,900 |
| NEPHGE 1B | 7.87 | 79,000 |
| NEPHGE 1C | 7.83 | 79,200 |
| NEPHGE 1D | 7.76 | 79,200 |
| NEPHGE 2 | 7.73 | 53,700 |
| NEPHGE 3 | 7.91 | 53,100 |
| NEPHGE 4 | 9.96 | 48,300 |
| NEPHGE 5 | 8.01 | 44,900 |
| NEPHGE 6 | 7.84 | 42,900 |
| NEPHGE 7 | 9.38 | 38,800 |
| NEPHGE 8 | 6.90 | 36,600 |
| NEPHGE 9 | 6.89 | 20,500 |
| NEPHGE 10 | 8.09 | 10,000 | where each number represents a single individual protein, the numbers marked A, B, C, or D representing variously modified forms of the same native protein, as well as modification and degradation products of these proteins. pI is the isoelectric point of the marker as determined by isoelectric focusing for acidic or neutral proteins and by non-equilibrium pH gradient gel electrophoresis for basic or neutral proteins, and molecular weight is the apparent molecular weight as determined by polyacrylamide gel electrophoresis. In a specific embodiment, the foregoing proteins are identified in heart biopsies cultured for 20 hours in vitro. In a preferred aspect of the invention, the markers IEF 1A, IEF 1B, IEF 6, IEF 7, IEF 8, NEPHGE 1A, NEPHGE 1B, NEPHGE 1C, NEPHGE 1D, NEPHGE 6, NEPHGE 9, and NEPHGE 10 are used in the methods of the invention.

The modified forms of a native protein may for example be glycosylated, phosphorylated, acetylated, methylated, or lipidified forms.

In this description and claims IEF stand for "isoelectric focusing", and NEPHGE stands for "non-equilibrium pH gradient electrophoresis."

In specific aspects, the present invention provides a number of methods for detecting the presence of an amount of a marker indicative of organ rejection, such as but not limited to biochemical analysis, immunological analysis, or by detecting the level of messenger RNA encoding the marker. An example of biochemical analysis is two-dimensional gel electrophoresis. Examples of immunological analysis include immunoblotting, enzyme-linked immunosorbent assay (ELISA), radio-immunoassay (RIA), immunofluorescence, agglutination, and immunoprecipitation.

In a specific embodiment, infra, a biopsy is labeled by incorporating a radioactive isotope (preferably [$^{35}$S]-methionine), by culturing the biopsy tissue in culture medium supplemented with [$^{35}$S]-methionine for about 20 hours. The proteins present in the tissue are subjected to 2D gel electrophoresis, after which the marker protein is identified on the gel, e.g., by comparison with a gel from a control sample (normal tissue biopsy or grade 0 rejection), and identification of protein spots not previously observed or that have much greater intensity in the sample from tissue undergoing or about to undergo rejection. The identification of the marker protein on the gels may be made by conventional exposure to X-ray film or, for example, by the use of phosphor imaging, which allows a much faster identification. Such analysis can be accomplished by eye, and preferably is accomplished using computer imaging.

According to the invention, any biological sample that contains the marker of the invention can be analyzed. Examples of such biological samples include, but are not limited to blood, serum, plasma, tissue biopsy, organ biopsy, synovial fluid, urine, bile fluid, cerebrospinal fluid, saliva, mucosal secretion, effusion, and sweat. It should be recognized that one or more of the markers may be present in soluble or solubilized form in such samples, or may be present in cells isolated with such samples. In the latter instance, the markers may be biosynthesized after isolation of the sample, thus providing an opportunity for biosynthetic labeling.

In a further aspect, the invention provides a test kit for evaluating the likelihood of organ rejection. The test kit of the invention provides means for detecting the presence of a marker indicative of organ rejection in a biological sample from a subject, wherein the marker is a protein expressed by cells in the organ suspected of being rejected; and means for determining whether the marker is present at an increased level relative to the level present in a corresponding biological sample from a normal subject or from the subject under observation prior to initiation of organ rejection phenomena. In one particular aspect, the means for detecting the presence of the marker and for determining whether the marker is present at an increased level comprise a specific binding partner of the marker; and means for detecting the level of binding of the specific binding partner of the marker to the marker. In still a further example, a kit of the invention provides a known amount of the marker to be detected, in which the marker provided in the kit is labeled.

In another embodiment, in a kit of the invention, a label for proteins expressed by cells present in the biological sample is provided, as are means for detecting the level of labeling of the marker, and correspondingly, the level of the marker.

In still another embodiment, the test kit comprises an oligonucleotide probe for mRNA encoding a marker expressed by cells present in the biological sample; and means for detecting the level of binding of the probe to the mRNA; wherein detection of and increased level of expression of the mRNA encoding the marker is indicative of an increased level of the marker.

In a preferred aspect, the test kit of the invention comprises means for detecting the presence of more than one marker indicative of organ rejection in a biological sample from a subject; and means for determining whether each marker is present at an increased level relative to the level present in a corresponding biological sample from a normal subject or at a subject prior to initiation of organ rejection phenomena.

The invention correspondingly provides markers of organ rejection in purified form. In preferred embodiments, the invention relates to the markers set forth above, which are related to heart allograft rejection. In specific embodiments, the invention provides a marker having a partial amino acid sequence selected from the group consisting of:

| IEF | SEQUENCE | (SEQ ID NO:) |
| --- | --- | --- |
| 1 | M L P Q L I P L L R V A | (SEQ ID NO:1) |
| 1 | (G) G H G F E G E | (SEQ ID NO:2) |
| 1 | K V A L P X S P N G | (SEQ ID NO:3) |
| 3 | X I A K G X G A G Y P K G I X T E X F | (SEQ ID NO:4) |
| 3 | (R) X Q Y I V T A M | (SEQ ID NO:5) |
| 3 | (N) D Q E V Q P X A V | (SEQ ID NO:6) |
| 3 | X X N E V X X I T X | (SEQ ID NO:7) |
| 5 | A L X Q N P T Q A E V L R | (SEQ ID NO:8) |
| 6 | X Q G Q V (A) H G D/R X X A P Y | (SEQ ID NO:9) |
| 6 | I V I Q V X L X N E M T G M | (SEQ ID NO:10) |
| 6 | X X M T N T V I X X | (SEQ ID NO:11) |
| 7 | A V Q E L E K | (SEQ ID NO:12) |
| 7 | I L A E R | (SEQ ID NO:13) |
| 7 | X E F V X V T K | (SEQ ID NO:14) |
| 7 | X X E E A V L V S L (N) | (SEQ ID NO:15) |
| 8 | M T F K A E I F K G P K V L E Q V X F X | (SEQ ID NO:16) |

The present invention advantageously provides for isolation of the marker proteins using routine techniques, such as excision from the two-dimensional gels, chromatography, immunoprecipitation, and the like.

The invention naturally extends to an antibody which specifically binds to a marker indicative of organ rejection in a biological sample from a subject suspected of being in danger of organ rejection, wherein the marker is a protein expressed by the cells in the organ suspected of being rejected. Such antibodies may be polyclonal antibodies or monoclonal antibodies, or an antigen-binding fragment thereof.

In a further aspect, the invention relates to a nucleic acid which encodes a marker indicative of organ rejection in a biological sample from a subject suspected of being in danger of organ rejection, wherein the marker is a protein expressed by the cells in the organ suspected of being rejected. In particular, the invention provides oligonucleotide probes or PCR primers specific for detecting the presence and level of such nucleic acids in a cell or cells in a biological sample from a subject expressing one or more markers of the invention. The invention further relates to nucleic acids useful for recombinant expression of such proteins, which are useful for diagnostic test kits and competitive immunoassay formats, or for testing for the presence of autoantibodies (e.g., in an ELISA format). DNA comprising a DNA sequence coding for a marker protein according to the invention also forms part of the invention. Such DNA will usually be isolated and may be recombinant. Recombinant DNA in accordance with the invention may be in plasmid, cosmid or phage. Vectors will frequently include one or more selectable markers to enable the selection of host cells transformed or transfected with them and, preferably, to enable selection of cells harboring vectors incorporating heterologous DNA. Appropriate start and stop signals will generally be present. Additionally, if the vector is intended for expression, sufficient regulatory sequences to drive expression will be included; vectors not including regulatory sequences are useful as cloning vectors. Cloning vectors can be introduced into *E. coli*, yeast, or any other suitable host, which facilitates their manipulation. Expression vectors can be introduced into host cells suitable for the expression of the protein. Although prokaryotic cells may be used, eukaryotic and, particularly, mammalian cells such as CHO cells may be preferred for this purpose. DNA in accordance with the invention can be prepared by any convenient method involving coupling together successive nucleotides, and/or ligating oligo- and/or poly-nucleotides, including in vitro processes, but recombinant DNA technology forms the method of choice. RNA coding for a marker protein according to the invention also forms part of the invention.

In a specific embodiment, the present invention provides a method of assaying a biological sample from a human being for the presence, and optionally the amount, of a marker protein according to the invention wherein proteins from said sample are distributed on a support matrix, after which said marker protein is identified on said matrix, optionally determining the amount of said marker protein by calibrating the assay with a preparation of said protein.

The biological sample may, for example, be a tissue solution of a biopsy or a sample of body fluid. The proteins of the sample may be distributed on various support matrices by methods specific to each matrix. Suitable matrices include, but are not limited to paper, cellulose acetate, silica, glass, carbon, sugars, plastics and derivatives thereof, and a person skilled in the art will be familiar with the techniques of using such support matrices for the separation of proteins.

As mentioned previously, measurement of elevated levels of one or more of the proteins which increase in expression as a prelude to or concomitant with organ rejection in a biopsy or body fluid from a patient having undergone organ transplantation would provide the potential or predictive evaluation of the rejection course. According to a further aspect of the invention, there is provided a method of predicting acute rejection in a human patient having undergone organ transplantation, which comprises assaying the relative amount of one or more of the marker proteins in a biopsy from the transplanted organ or in a sample of body fluid from the patient by any of the methods described above to determine whether said protein or proteins are over-expressed. The amount of marker protein present need not be determined absolutely; it will often be sufficient to compare the amount of marker protein detected in the individual with that detected in a control (normal, healthy) individual.

It is conceivable that one or more of the marker proteins are over-expressed in connection with rejection episodes following human transplantation of other organs such as for example lung, liver, skin, or kidney.

Also, it is conceivable that one or more of the marker proteins are over-expressed in connection with rejection of other transplanted organs, such as but not limited to lung, liver, and kidney. Over-expression of one or more marker proteins may also accompany inflammation or diseases in various organ systems of the human body, such as acute myocardial infarction, hypertension, cardiomyopathy, and organ-specific autoimmune diseases, including but not limited to autoimmune (Hasimoto's) thyroiditis, hyperthyroidism (e.g., Grave's disease), type I diabetes melitis, insulin-resistant diabetes, autoimmune adrenal insufficiency (Addison's disease), autoimmune oophoritis, autoimmune orchitis, autoimmune hemolytic anemia ("warm" autoantibody type and cold agglutinin disease), paroxysmal cold hemoglobinuria, autoimmune thrombocytopenia, autoimmune neutropenia, pernicious anemia, pure red cell anemia, autoinmune coagulopathies, myasthenia gravis, autoimmune polyneuritis, multiple sclerosis, pemphigus and other bullous diseases of the skin, rheumatic carditis, Goodpasture's syndrome, postcardiotomy syndrome (Dressier's syndrome), ulcerative colitis, inflammatory bowel disease, glomerulonephritis, and rheumatic fever, as well as systemic autoimmunie diseases such as rheumatoid arthritis, Sjögren's syndrome, polymyositis, dermatomyositis, scleroderma, and systemic lupus erythematosus. Accordingly, the present invention further provides a method for the diagnosis of the above mentioned diseases, which comprises assaying the relative amount of one or more of the marker proteins in a biopsy from the suspected organ or in a sample of body fluid from the patient by any of the methods described above to determine whether said protein or proteins are over-expressed.

When the amino acid sequences of the marker proteins comprised by this invention are known, it is possible to synthesize DNA or RNA probes which may be used for:

i) direct detection of DNA and RNA expressing said marker proteins on a fixed or frozen tissue section using e.g. chromogenous, chemiluminescent or immunofluorescent technique; and ii) polymerase chain reaction (PCR).

Polyclonal and monoclonal antibodies to the marker proteins comprised by the invention can also be used to guide drugs to the site at which the drug should work (so-called targeted drugs). Accordingly, in a further aspect, the present invention provides a method of treating a human being by the administration of drugs wvlhich are guided specifically to the desired site of action by coupling to antibodies which recognize any of said marker proteins. The coupling of the drug to the antibody can be direct covalent coupling or indirect, for example, the encapsulation of the drug in a liposome and the attachment of the antibody to the liposome. In this respect, the word "drug" should be understood as any compound which can modulate cellular biochemistry. A list of suitable drugs would thus include, but is not limited to pharmaceutically active substances, DNA or RNA sense/antisense drugs and even substances which would modify the behavior of other cells in the vicinity of the binding site for the targeted drug.

Accordingly, it is a primary object of the present invention to provide for the diagnosis and prognosis of organ rejection.

It is a particular object of the invention to provide for the diagnosis and prognosis of allograft rejection.

It is a more particular object of the invention to provide for specific and sensitive diagnosis of impending rejection of a transplanted heart.

Yet another object of the invention is to identify and provide markers associated with rejection phenomena.

Still another object of the invention is to provide antibodies to the markers.

A further object of the invention is to provide nucleic acids encoding such markers, or portions of such markers encoded by 10 or more nucleotides.

These and other objects of the present invention will be further appreciated by reference to the following Drawings and Detailed Description of the Invention.

DETAILED DESCRIPTION OF THE INVENTION

Figure 1:
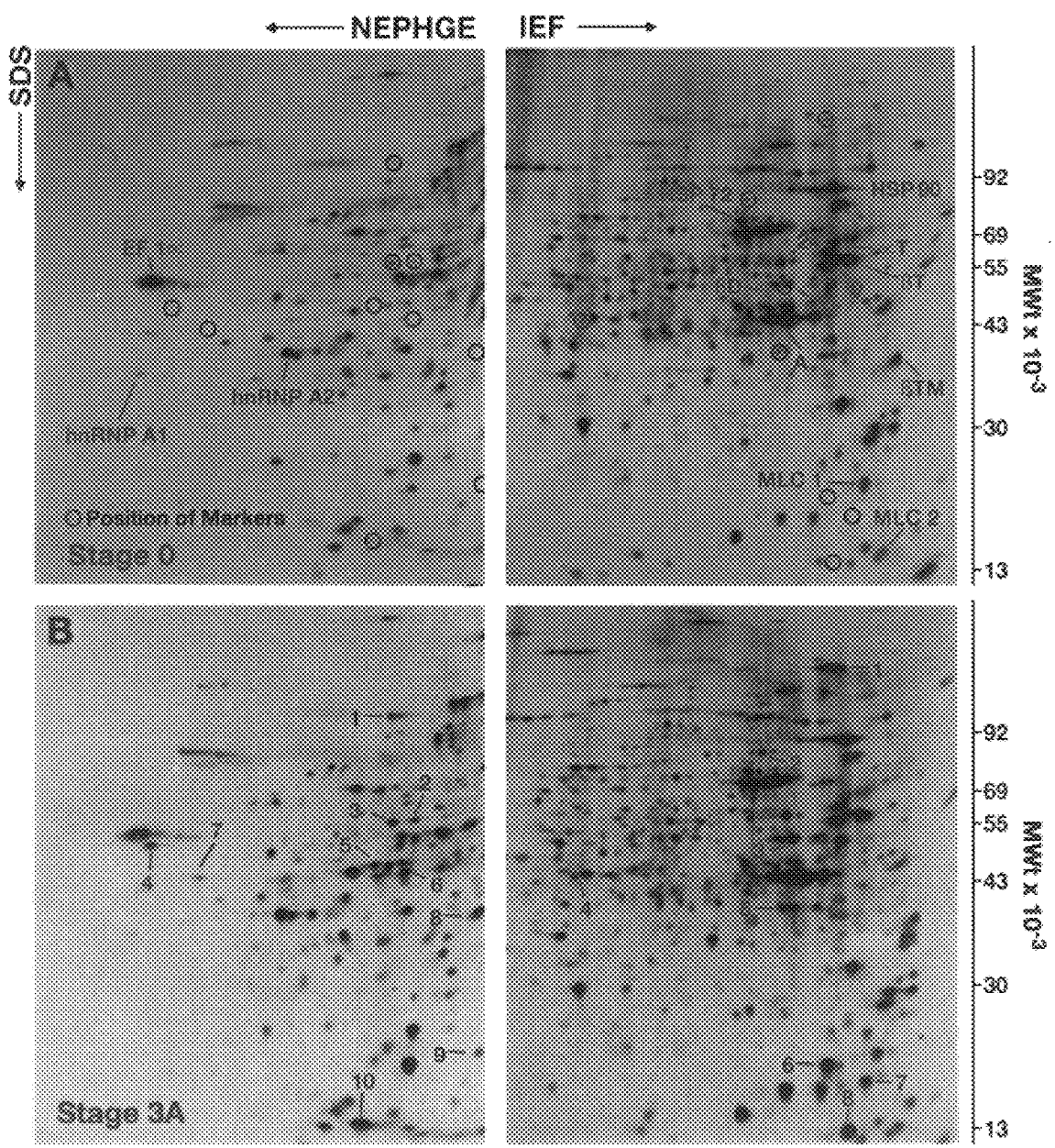
FIG. 1. Two-dimensional gel electrophoresis of endomyocardial biopsies. (A) Fluorogram from a biopsy having rejection grade 0. (B) Fluorogram from a biopsy having rejection grade 3A. The gels were prepared as described in EXAMPLE 1, infra. Briefly, biopsies were labeled in methionine-free DMEM supplemented with [$^{35}$S]-methionine by incubation for 20 hrs at 37° C., 5% $CO_2$, humidified atmosphere, homogenized, and loaded on both an isoelectric focusing (IEF) and a non-equilibrium pH gel electrophoresis (NEPHGE) gel for first dimension analysis. The gels were extruded and run in the second dimension on a 12.5% polyacrylamide gel. The gels 2-D gels were fixed for 45 min. treated with AMPLIFY®, dried, and exposed to X-ray film at −70° C. for five days. pI and MW values were assigned by comparison against the creatine phosphokinase (CPK) pI markers (British Drug House) and known molecular weight HeLa proteins. In particular, in FIG. 1, the landmark proeins in panel (A) for the IEF gel are heat shock proteins 90 and 72 (HSP90 and HSP72), α- and β-tubulin (αT and βT), vimentin (V), intermediate filament associated proteins 24 and 35; α- and β-desmin (αD and βD), actin (A), β-tropomyosin (βTM), and myosin light chains 1 and 2 (mlc1 and mlc2). In panel (A) for the NEPHGE gel are elongation factor 1α (EF1α), and the heterogenious nuclear ribonuclear proteins A1 and A2 (hnRNP A1 and hnRNP A2). Numbered arrows in panel (B) indicate the marker proteins.

As noted above, the present invention relates to the diagnosis and prognosis of organ rejection in a subject suspected of being at risk for organ rejection, e.g., allograft rejection, xenograft rejection, graft versus host disease, or autoimmune disease.

Accordingly, various terms are used throughout the specification, which are defined herein.

The term "organ rejection" is used herein to refer to immune-mediated or inflammatory destruction of an organ. Most frequently, organ rejection occurs following allograft or xenograft transplantation. However, the term "organ rejection" as used herein encompasses autoimmune organ rejection, e.g., pericarditis, and graft-versus-host mediated rejection.

The term "organ" refers to any part of the body exercising a specific function, such as but not limited to, the heart, lungs, liver, kidneys, skin, pancreas, thyroid, brain, stomach, intestines, testes, and ovaries, and also includes glands such as the adrenal glands, pancreatic islets, and the like. The most commonly transplanted organs are heart, liver, kidneys, lungs, and skin, although transplantation of other organs or glands is within the scope of the invention.

The term "allogeneic" or "allograft" refers to transplantation of an organ from the same species of animal. Presently, "allogeneic" transplants are preferred, with closest possible tissue typing (the greatest number of histocompatibility antigens in common between the donor and recipient) more preferred. However, "xenogeneic" transplants, that is, transplantation of organs from other species of animal into a human, e.g., with hearts from transgenic pigs, are also contemplated by the present invention.

The term "marker" is used herein to refer to a protein that demonstrates increased levels of expression preceding or during organ rejection. Preferably, such proteins are not lymphocyte or leukocyte-associated proteins, including such proteins as soluble cell surface markers (e.g., soluble IL-2 receptor, soluble CD-4, soluble CD-8, and soluble T cell antigen receptor) or lymphokines or cytokines associated with immune or inflammatory responses. More preferably, a marker of the invention is a protein found in the tissue of the rejected organ prior to onset of a rejection episode. Expression of a marker of the invention is not influenced by the immunosuppressive treatment administered with allograft transplantation. In a specific embodiment, the markers of the invention are not tumor necrosis factor-α or lymphotoxin (tumor necrosis lactor-β).

The markers of the invention are proteinaceous molecules, and as such, may be modified by the cells that express them. As noted in the Examples, infra, various slightly modified forms of markers have been observed. In some cases, partial sequence data confirms that spots having only slight variation in molecular weight, isoelectric point, or both, represent variously modified forms of the same protein. As discussed in detail, infra, such modifications include, but are not limited to, glycosylation differences, phosphorylation, N-terminal acetylation, C-terminal amidation, mRNA splicing variations, and the like.

The term "acute rejection" as used herein is defined as the presence of rejection grade 3A or greater as determined by pathological evaluation. This is based on the scale published first by Caves et al. (1973, J. Thorac. Cardiovasc. Surg. 66:461–66) and subsequently modified by Billingham et al. (1990, J. Heart Transplant. 9:587–593) to include the grades 0 (no rejection), 1A, 1B, 2, 3A, and 4.

The term "likelihood of organ rejection" refers to the probability of a rejection episode, which can be predicted based on the level of expression of a marker or markers of the invention.

As used herein, the term "biological sample" refers to a tissue or body fluid obtained from a subject. Examples of biological samples include, but are by no means limited to, blood, serum, plasma, tissue biopsy, organ biopsy, synovial fluid, urine, bile fluid, cerebrospinal fluid, saliva, mucosal secretion, effusion, and sweat.

The term "subject" preferably refers to a human subject, but also includes animals such as, but not limited to, domesticated mammals (dogs, cats, sheep, cows, horses, goats, pigs, etc.), wild animals held in captivity, and wild animals treated in the wild.

The term "biochemical analysis" as used herein refers to analysis based on the determination of physical-chemical characteristics of putative markers, including but not limited to apparent molecular weight by polyacrylamide gel electrophoresis (under both denaturing and non-denaturing conditions) and mass spectrometry, isoelectric point as determined by isoelectric focusing, non-equilibrium pH gradient gel electrophoresis, or chromatography, relative hydrophobicity as determined by partition coefficient or reverse-phase chromatography, amino acid composition, carbohydrate composition, and partial or complete amino acid sequence. Typically, and in a specific embodiment, infra, biochemical analysis will involve characterizing bands on a one-dimensional gel, or more preferably, spots on a two-dimensional gel.

The term "immunological analysis" refers to characterization of the markers of the invention on the basis of immunospecific binding, i.e., reactivity with a specific binding partner of the marker. The paradigm of a specific binding partner is an antibody, however, the invention contemplates use of specific receptors or other binding partners of the markers, where such demonstrate specific, high affinity binding analogous to binding of an antibody. Accordingly, any techniques applicable to antibody binding to a marker extend to binding of any specific binding partner of a marker to the marker. Examples of immunological analysis techniques include, but are not limited to immunoblotting, enzyme-linked immunosorbent assay (ELISA), radio-immunoassay (RIA), agglutination, immunofluorescence, immunochemiluminescence, immunochromatography, biosensor, optical sensor, and immunoprecipitation.

The term "antigenic" as used herein means capable of specific immunological recognition. Example of immune recognition include antibody binding and recognition by the T cell antigen receptor (when the antigen is presented in the context of a major histocompatibility molecule). An antigenic polypeptide will usually contain at least five, and preferably at least 10, amino acids in the antigenic determinant (other molecules, such as nucleic acids and oligonucleotides may have antigenic determinants of equivalent size, although the subunits will be nucleotide and sugar residues, respectively).

As used herein, "detecting the level of messenger RNA" refers to Northern analysis, reverse-transcriptase PCR (RT-PCR), ini vitro expression, and comparable means for detecting the presence of RNA encoding a marker of the invention.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Marker Proteins

A marker protein of the invention is a protein expressed by cells in organs undergoing rejection. The marker proteins are expressed at very low levels in samples from normal (donor) organs or from organs prior to rejection episodes, which indicates that the markers are not expressed by cells that infiltrate the organ during rejection. Moreover, two-dimensional gel analysis with biosynthetic labeling of resting and PMA activated lymphocytes demonstrates that the levels of expression of these markers are not increased by stimulation of lymphocytes in vitro. However, the markers may be produced by cells of the organ, e.g., myocytes in the heart, by migrating cells that are resident in the organ, e.g., blood borne fibroblastic cells, or even by pre-located lymphocytes or leukocytes. As noted above, the level of expression of a marker protein of the invention increases in association with impending or onset of organ rejection, particularly acute rejection.

A marker protein according to the invention may be obtained in a variety of ways. First, it may be isolated by 2D electrophoresis of endomyocardial biopsies in IEF and NEPHGE gels, excision of the proper spot on the gels and extraction of the protein therefrom. Second, it may also be found in human serum and plasma, from which it can be purified, for example by affinity chromatography. Third, it may be prepared by culturing either cells which naturally produce said protein, or cells which are modified to produce said protein (such as Chinese hamster ovary (CHO), or other suitable host cells transformed or transfected to express the marker protein) and recovering the expressed protein from the culture. For example, the protein may be extracted from the cells by means of a detergent or salt buffer. Detergents used may for example be anionic or nonionic or a mixture thereof. The proteins to which microsequences are provided are insoluble by 3×10 min washes in Hank's buffer alone. All the marker proteins can be solubilized in for, example, lysis buffer (9.5 M urea, 2% NONIDET P-40® (NP-40), 2% ampholytes, and 5% 2-mercaptoethanol) or sample buffer (2% sodium dodocyl sulfate (SDS), 5% 2-mercaptoethanol, 10% glycerol, and 60 mM Tris-HCl, pH 6.8). It may also be possible to modify the culturing conditions in such a way that the protein is exported from the cells and may be isolated from the culture medium. For example, the DNA vector used for the transformation or transfection of the host cells may include a signal sequence directing the export of the protein from the cells.

Purification of a marker protein according to the invention, however obtained, can be achieved by any suitable method. In a specific embodiment, infra, the marker proteins are purified by two-dimensional gel electrophoresis. These purified proteins are used further for microsequencing, or alternatively, can be cut out of the gel and used for immunization. A preferred technique is affinity chromatography, which may be performed by the following steps:

(a) providing a crude source of said protein (for example, the supernatant of cells expressing said protein);

(b) introducing the crude source to an affinity matrix containing immobilized specific binding molecules for said protein and permitting said protein to bind to the matrix;

(c) washing the matrix to remove unbound contaminants;
(d) recovering said protein in substantially pure form by elution from the matrix.

Affinity columns can be prepared in a number of ways well known to those skilled in the art. Specifically, binding molecules which have an affinity for a marker protein according to the invention may include polyclonal and monoclonal antibodies against said protein. Cyanogen bromide-activated SEPHAROSE®, for example, can readily be used to couple antibodies or other specific binding molecules.

In a specific aspect, an antibody to a known protein, in particular a monoclonal antibody, that cross reacts with a marker of the invention may be used to immunoaffinity purify or immunoprecipitate the marker. For example, it may be possible to use a monoclonal or polyclonal antibody to myosin light chain to isolate IEF 5.

In specific embodiments, the marker proteins are the proteins characterized in the Examples herein by molecular weight and isoelectric point (Table 1, infra), partial amino acid sequence information (Table 3, infra), or both.

Nucleic Acids Encoding the Markers

In accordance with the present invention, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Haines & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra).

The conditions of temperature and ionic strength determine the "stringency" of the hybridization. For preliminary screening for homologous nucleic acids, low stringency hybridization conditions, corresponding to a $T_m$ of 55°, can be used, e.g., 5× SSC, 0.1% SDS, 0.25% milk, and no formamide; or 30% formamide, 5× SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6× SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; more preferably at least about 15 nucleotides; most preferably the length is at least about 20 nucleotides.

As used herein, the term "sequence homology" in all its grammitical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammitical forms refers to the degree of identity or correspondence between nucleic acid or amino acid sequences of proteins that do not share a common evolutionary origin (see Reeck et al., supra).

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed oil the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The present invention contemplates isolation of a gene encoding an antigenic portion of a marker of the invention, including a full length, or naturally occurring form of the marker, and any antigenic fragments thereof from any animal, particularly mammalian or avian, and more particularly human, source. As used herein, the term "gene" refers to an assembly of nucleotides that encode a polypeptide, and includes cDNA and genomic DNA nucleic acids.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

A gene encoding marker, whether genomic DNA or cDNA, can be isolated from any source, particularly from a human cDNA or genomic library. Methods for obtaining the marker gene are well known in the art, as described above (see, e.g., Sambrook et al., 1989, supra). In a specific aspect of the invention, a gene encoding a marker is isolated using an expression library, e.g., a λgt11 expression library with an antibody to the marker prepared as described infra.

Accordingly, any animal cell potentially can serve as the nucleic acid source for the molecular cloning of a marker gene. The DNA may be obtained by standard procedures known in the art from cloned DNA (e.g., a DNA "library"), and preferably is obtained from a cDNA library prepared from the organ under consideration (e.g., a heart cDNA library for heart rejection markers), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired marker gene may be accomplished in a number of ways. For example, if an amount of a portion of a marker gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). For example, a set of oligonucleotides corresponding to the partial amino acid sequence information obtained for the markers can be prepared and used as probes for DNA encoding the markers, or as primers for CDNA or mRNA (e.g., in combination with a poly-T primer for RT-PCR). Preferably, a fragment is selected that is highly unique to the marker of the invention. Those DNA fragments with substantial homology to the probe will hybridize. As noted above, the greater the degree of homology, the more stringent hybridization conditions can be used. In a specific embodiment, low stringency hybridization conditions are used to identify a homologous marker.

Further selection can be carried out on the basis of the properties of the gene, e.g., if the gene encodes a protein product having the isoelectric, electrophoretic, amino acid composition, or partial amino acid sequence of a marker protein as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoretic behavior, proteolytic digestion maps, or antigenic properties as known for marker. (The antibodies to marker proteins, described in detail infra, can be used to confirm expression of the marker.)

A marker gene of the invention can also be identified by mRNA selection, i.e., by nucleic acid hybridization followed by in vitro translation. In this procedure, nucleotide fragments are used to isolate complementary mRNAs by hybridization. Such DNA fragments may represent available, purified marker DNA, or may be synthetic oligonucleotides designed from the partial amino acid sequence information. Immunoprecipitation analysis or functional assays (e.g., tyrosine phosphatase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against a marker.

A radiolabeled marker cDNA can be synthesized using the selected mRNA (from the adsorbed polysomes) as a template. The radiolabeled mRNA or cDNA may then be used as a probe to identify homologous marker DNA fragments from among other genomic DNA fragments.

The present invention also relates to cloning vectors containing genes encoding analogs and derivatives of the marker of the invention, that have the same or homologous functional activity as marker, and homologs thereof from other species. The production and use of derivatives and analogs related to marker are within the scope of the present invention. In a specific embodiment, the derivative or analog is functionally active, i.e., capable of exhibiting one or more functional activities associated with a full-length, wild-type marker of the invention, which may or may not be the actual biochemical role of the marker. For example, the derivative or analog could have decreased antigenicity or increased stability in the conditions in which it may be employed.

Marker derivatives can be made by altering encoding nucleic acid sequences by substitutions, additions or deletions that provide for functionally equivalent molecules. Preferably, derivatives are made that have enhanced or increased functional activity, e.g., anitigenicity or stability, relative to the native marker.

Due to the degeneracy of nucleotide coding sequences, other DNA sequences which encode substantially the same amino acid sequence as a marker gene may be used in the practice of the present invention. These include but are not limited to allelic genes, homologous genes from other species, and nucleotide sequences comprising all or portions of marker genes which are altered by the substitution of different codons that encode the same amino acid residue within the sequence, thus producing a silent change. Likewise, the marker derivatives of the invention include, but are not limited to, those containing, as a primary amino acid sequence, all or part of the amino acid sequence of a marker protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis. For situations where one charged amino acid is exchanged with another (similarly or differently charged, or uncharged) amino acid, the changes in pI will be more readily detectable in small proteins whose pI falls within the interval between the pKas of the groups involved. Such a change may be imperceptible for large proteins.

The genes encoding marker derivatives and analogs of the invention can be produced by various methods known in the art. The manipulations which result in their production can occur at the gene or protein level. For example, the cloned marker gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of marker, care should be taken to ensure that the modified gene remains within the same translational reading frame as the marker gene, uninterrupted by translational stop signals, in the gene region where the desired activity is encoded.

Additionally, the marker-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated marker gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E.*

*coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. Coli* plasmid with sequences from the yeast 2µ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of Marker Polypeptides

The nucleotide sequence coding for a marker, or antigenic fragment, derivative or analog thereof, can be inserted into an appropriate expression vector, i.e., a vector which contains the necessary elements for the transcription and translation of the inserted protein-coding sequence. Such elements are termed herein a "promoter."

Thus, the nucleic acid encoding the marker of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding a marker and/or its flanking regions.

In another embodiment, chimeric marker polypeptide fragments can be prepared, e.g., a glutathione-S-transferase (GST) fusion protein, a maltose-binding (MBP) protein fusion protein, or a poly-histidine-tagged fusion protein, for expression in bacteria. Expression of a marker or an antigenic fragment thereof as a fusion protein can facilitate stable expression, or allow for purification based on the properties of the fusion partner. For example, GST binds glutathione conjugated to a solid support matrix, MBP binds to a maltose matrix, and poly-histidine chelates to a Ni-chelation support matrix. The fusion protein can be eluted from the specific matrix with appropriate buffers, or by treating with a protease specific for a cleavage site usually engineered between the marker polypeptide and the fusion partner (e.g., GST, MBP, or poly-His).

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. Eukaryotic expression systems, especially higher eukaryotic systems, are preferred because they are capable of modifying the protein product in a manner closer or identical to the native molecule in vivo. The expression elements of vectors vary in their strengths and specificities. Depending on the host-vector system utilized, any one of a number of suitable transcription and translation elements may be used.

A recombinant marker of the invention, or functional fragment, derivative or analog thereof, may be expressed chromosomally, after integration of the marker coding sequence by recombination. In this regard, any of a number of amplification systems may be used to achieve high levels of stable gene expression (See Sambrook et al., 1989, supra).

The cell into which the recombinant vector comprising the nucleic acid encoding the marker is cultured in an appropriate cell culture medium under conditions that provide for expression of the marker by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a marker protein may be controlled by any promoter/enhancer element known in the art, but these regulatory elements must be functional in the host selected for expression. Promoters which may be used to control marker gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals.

Expression vectors containing a nucleic acid encoding a marker of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a marker is inserted within the "selection marker" gene sequence of the vector, recombinants containing the marker insert can be identified by the absence of the marker gene function. In the fourth approach, recombinant expression vectors can be identified by assaying for the activity, biochemical, or immunological characteristics of the gene product expressed by the recombinant, provided that the expressed protein assumes a functionally active conformation.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, the transmembrane marker protein expressed in bacteria may not be properly folded. Expression in yeast can produce a glycosylated product. Expression in eukaryotic cells can increase the likelihood of "native" glycosylation and folding of a heterologous protein. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

A recombinant marker protein expressed as an integral membrane protein can be isolated and purified by standard methods. Generally, the integral membrane protein can be obtained by lysing the membrane with detergents, such as but not limited to, sodium dodecyl sulfate (SDS), Triton X-100, nonidet P-40 (NP-40), digoxin, sodium deoxycholate, and the like, including mixtures thereof.

Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

The present invention further provides for characterizing a marker of the invention. In one embodiment, the marker can be purified from natural sources. In a specific embodiment, infra, the markers purified from 2-dimensional yield partial amino acid sequence information. Alternatively, once a recombinant which expresses the marker gene sequence is identified, the recombinant marker product, which can be produced in relatively large quantities, can be analyzed. This is achieved by assays based on the physical or functional properties of the product, including radioactive labelling of the product followed by analysis by gel electrophoresis, immunoassay, etc.

The structure of marker of the invention can be analyzed by various methods known in the art. Structural analysis can be performed by identifying sequence similarity with other known proteins. The degree of similarity (or homology) can provide a basis for predicting structure and function of marker, or a domain thereof. In a specific embodiment, sequence comparisons can be performed with sequences found in GenBank, using, for example, the FASTA and FASTP programs (Pearson and Lipman, 1988, Proc. Natl. Acad. Sci. USA 85:2444–48).

In specific embodiments, infra, partial amino acid sequence information from various marker proteins is obtained by well known microsequencing techniques. The partial sequence information is compared with known sequences in the databases. In some instances, there is no significant sequence similarity or homology (less than 75% match) of the marker protein with a known protein sequence, which indicates that the marker protein is a unique protein. In other instances, the marker protein demonstrates at least a 75% match, and in some instances, at least a 90% match, with known proteins. It should be understood, however, that the degree of similarity of partial amino acid sequence information is only a rough indicator of the relationship between the marker protein and the known protein. For example, it is well known that a family of proteins or protein domains found on diverse proteins can have stretches of sequence similarity (or homology) approaching 100%.

Preferably, a marker of the invention is characterized based on more than one partial amino acid sequence. As reported in an example, infra, some of the markers have partial amino acid sequences that show similarity or homology to one or more diverse proteins. In a specific embodiment, infra, a comparison of three partial amino acid sequences of a marker protein (IEF 3) shows similarity with rat and human insulin responsive glucose transporter type 4, a second partial amino acid sequence shows similarity with human transcription factor 7 and angiotensin converting enzyme precursor, and a third partial sequence has no significant similarity with a known protein. Thus, this protein appears to be unique, i.e., its sequence has not been determined previously.

Furthermore, partial amino acid sequence information is only one element of analysis of the marker proteins. In a specific embodiment, infra, a marker protein (IEF 5) shows a 92.3% match with ventricular myosin light chain. However, the molecular weight of the marker (about 39,200 Daltons) is much higher than the molecular weight of myosin light chain (about 22,000 Daltons). Thus, a marker may be a novel protein with a high degree of similarity to a known protein.

For N- or C-terminal amino acid sequencing, it is possible that partial amino acid sequence information may correspond to sequences of more than one protein, but this would produce multiple amino acid residues at each position if more than one protein were indeed present. An alternative, to avoid N-terminus blocking, is to use polypeptide fragmentation (using for example trypsin cleavage), followed by separation of the peptides (e.g., by HPLC). The number of the fragments gives an indication of whether one or two proteins were present in the sample. In the Example herein, two dimensional gel electrophoresis provides a very high degree of purification of the polypeptide that is subsequently used for microsequencing. Also, the partial amino acid sequences may include un-assigned residues, or may have artifacts (deletions or insertions), thus affecting the accuracy of a quantitative evaluation of sequence similarity. Nevertheless, the partial amino acid sequence information is highly informative for characterizing a marker protein.

The protein sequence can be further characterized by a hydrophilicity analysis (e.g., Hopp and Woods, 1981, Proc. Natl. Acad. Sci. U.S.A. 78:3824). A hydrophilicity profile can be used to identify the hydrophobic and hydrophilic regions of the marker protein.

Secondary structural analysis (e.g., Chou and Fasman, 1974, Biochemistry 13:222) can also be done, to identify regions of marker that assume specific secondary structures.

Manipulation, translation, and secondary structure prediction, as well as open reading frame prediction and plotting, can also be accomplished using computer software programs available in the art.

By providing an abundant source of recombinant marker, the present invention enables quantitative structural determination of marker, or domains thereof. In particular, enough material is provided for nuclear magnetic resonance (NMR), infrared (IR), Raman, and ultraviolet (UV), especially circular diclhroisin (CD), spectroscopic analysis. In particular NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed. These include but are not limited to X-ray crystallography (Engstom, A., 1974, Biochem. Exp. Biol. 11:7–13). Computer modeling can also be used, especially in connection with NMR or X-ray methods (Fletterick, R. and Zoller, M. (eds.), 1986, Computer Graphics and Molecular Modeling, in *Current Communications in Molecular Biology*, Cold Spring Harbor Laboratory, Cold Spring Harbor, N.Y.).

In yet a further embodiment, a putative marker of the invention can be tested to determine whether it cross-reacts with an antibody specific for a related marker, or another protein. For example, the marker IEF 5 can be reacted with an antibody specific for myosin light chain to determine if there is cross reactivity. Alternatively, a marker can be used to generate antibodies, which can be tested for cross reactivity with marker. For example, antibodies generated to IEF 5 can be generated and used to test for cross reactivity with myosin light chain. The degree of cross reactivity provides information about structural homology or similarity of proteins.

Antibodies to the Markers

According to the invention, marker produced recombinantly or by chemical synthesis, and fragments or other derivatives or analogs thereof, including fusion proteins, may be used as an immunogen to generate antibodies that recognize the marker. Such antibodies include but are not limited to polyclonal, monoclonal, chimeric, single chain, Fab fragments, and an Fab expression library.

Various procedures known in the art may be used for the production of polyclonal antibodies to a recombinant marker or derivative or analog thereof. For the production of antibody, various host animals can be immunized by injection with the marker, or a derivative (e.g., fragment or fusion protein) thereof, including but not limited to rabbits, mice, rats, sheep, goats, chickens, etc. Immunization of chickens may be preferred as this species of animal is much more distantly related to humans or mammals in general, and thus may be expected to have a more robust immune response as the homologous chicken marker proteins are likely to be less homologous.

In one embodiment, the marker or fragment thereof can be conjugated to an immunogenic carrier, e.g., bovine serum albumin (BSA) or keyhole limpet hemocyanin (KLH). Various adjuvants may be used to increase the immunological response, depending on the host species.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and BCG (*bacille Calmette-Guerin*) and *Corynebacterium parvum*. Preferably, the adjuvant is pharmaceutically acceptable. Certain adjuvants are useful for experimental purposes in laboratory animals (rats, mice, rabbits, etc.), such as but not limited to Freund's (complete and incomplete), mineral gels such as aluminum hydroxide, surface active substances such as lysolecithin, pluronic polyols, polyanions, peptides, oil emulsions, keyhole limpet hemocyanins, and dinitrophenol. Other adjuvants are acceptable for veterinary use, including mineral gels. Adjuvants for use in humans are restricted because of potential deliterious effects, e.g., of Freund's adjuvants, and include potentially useful human adjuvants such as alum and BCG (*bacille Calmette-Guerin*) and *Corynebacterium parvum*.

For preparation of monoclonal antibodies directed toward the marker, or fragment, analog, or derivative thereof, any technique that provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al. 1985, Nature 314:452–454) by splicing the genes from a mouse antibody molecule specific for a marker together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogeneic antibodies to induce an immune response, in particular an allergic response, themselves.

According to the invention, techniques described for the production of single chain antibodies (U.S. Pat. No. 4,946,778) can be adapted to produce marker-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for a marker, or its derivatives, or analogs.

The invention further contemplates isolation and use of autoantibodies to the markers. The possibility exists that some transplanted patients will naturally develop antibodies to one or more of the marker proteins comprised by this invention. In addition, certain patients with auto-immune diseases could develop antibodies to one or more of these proteins. In either case, these human antibodies directed against any one of the marker proteins could easily be isolated from a blood sample and purified by techniques known to one skilled in the art, e.g., by immunoaffinity purification using the recombinant or natural marker as an affinity agent. These human antibodies could be employed in an assay method according to the invention in the same manner as antibodies derived from any other animal species and thus, for the purposes of this disclosure, are considered equivalent.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a marker, one may assay generated hybridomas for a product which binds to a marker fragment containing such epitope. For selection of an antibody specific to a marker from a particular species of animal, one can select on the basis of positive binding with marker expressed by or isolated from cells of that species of animal.

The foregoing antibodies can be used in methods known in the art relating to the localization and activity of the marker, e.g., for Western blotting, imaging marker in situ, measuring levels thereof in appropriate physiological samples, etc.

In preferred aspect, the immunoassay employed is an immunochromatographic assay. Such a device comprises a solid phase means for conducting a liquid. As used herein, the term "solid phase means for conducting a liquid" refers to a solid support that allows migration of a liquid therethrough, e.g., via capillary action. Many immunochromatographic assay means and formats are known in the art, and can be used in the practice of the present invention. Immunochromatographic assays using a membrane as a solid support in a dipstick or flow-through device are well established for use in the clinical laboratory and for alternative, i.e., non-laboratory, site testing. The usual presentation for an immunochromatographic assay device is a membrane (cellulosic or non-cellulosic) enclosed in a plastic holder. The plastic holder keeps the membrane in a suitable configuration in order to ensure correct functioning of the entire device. There are many variations of the basic structure of assay devices. For example, Litman et al. (U.S. Pat. No. 5,156,952 and U.S. Pat. No. 5,030,558) describe an assay method and device for determining the presence of a minimum amount of an analyte in a sample. Ullman et al. (U.S. Pat. Nos. 5,137,808 and 4,857,453) describe an device to house an assay membrane that includes self-contained liquid reagents to aid sample flow. Dafforn et al. (U.S. Pat. No. 4,981,768) describes a device with ports for applying sample and extra liquid. Assay devices are also described by Corti et al. (European Patent Application No. 89118378.2), Greenquist et al. (U.S. Pat. No. 4,806,312), Berger et al. (U.S. Pat. No. 5,114,673), Kromer et al. (EP-A 0 229 359), Jackowski (U.S. Pat. No. 5,290,678), Tom et al. (U.S. Pat. No. 4,366,241), Zuk (EP-A 0 143 574), Bernstein (U.S. Pat. No. 4,770,853), May et al. (WO 88/08534), Ching et al. (EP-A 0 299 428)and Valkirs et al. (U.S. Pat. No. 4,632,901), each of which is incorporated herein by reference in its entirety.

Preferably, the immunochromatographic assay means includes a control to indicate that the assay has proceeded correctly. The control can be a specific binding spot more distal from the sample application point on the solid phase support than the detection zone that will bind to labeled reagent in the presence or absence of analyte, thus indicating that the mobilizable receptor has migrated a sufficient distance with the liquid sample to give a meaningful result. Suitable labels for use in immunochromatographic assays include enzymes, fluorophores, chromophores, radioisotopes, dyes, colloidal gold, latex particles, and chemiluminescent agents. When a control marker is employed, the same or different labels may be used for the receptor and control marker, which described a reagent delivery system comprising a matrix saturated with a reagent or components thereof dispersed in a water soluble polymer for controlling the dissolution rate of the reagent for delivery to a reaction matrix positioned below the matrix.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radio lable, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Quantitation is required to some degree to determine whether a marker is present at a level above the threshold level. However, immunochromatographic assays can be formatted to be semiquantative. The term "semiquantitative" refers to the ability to discriminate between a level that is above the threshold, and a level that is not above the threshold. Accordingly, the invention contemplates immunochromatographic assays that yield a positive result when the level of the marker is statistically greater than the level in a normal or grade 0 organ.

Diagnosis and Prognosis of Organ Rejection

The term "diagnosis" means the determination of the nature of a disease. The present invention, because it relies upon detection of markers associated with and expressed by the cells of an organ, is a sensitive and accurate diagnostic indicator of organ rejection. In contrast to markers of general immune activation, which can be indicative of viral, bacterial, or parasitic infection as well as organ rejection, the markers of the present invention specifically relate to organ rejection. Accordingly, the markers of the invention advantageously provide for differential diagnosis of a subject believed to be at risk for organ rejection, but in whom immune activation may relate to an infection.

It is readily apparent that initiating immunosuppressive therapy in an organ transplant recipient with elevated immune markers due to a viral infection is counter-productive, and quite possibly harmful. Accordingly, in a specific aspect, detection of an elevated level of one, or preferably more, of the markers of the invention can differentially diagnose organ rejection from helpful immune activation.

The term "prognosis" means the forecast of a probable course and outcome of a disease, disorder, or medical procedure. The present invention provides an accurate prognostic indicator of the likelihood of transplant survival, as well as the course and severity of organ rejection, whether due to host-versus-graft disease or autoimmune disease.

As noted above, early diagnosis of rejection is essential to keep the patient in a state of stable non-rejection, avoiding advanced states of destructive rejection. Because changes in protein expression must precede histological, immunological, and functional responses, the present invention takes a new approach to predict acute rejection based on protein analysis of a biological sample from a subject. In a specific example, infra, endomyocardial biopsies are analyzed by 2D gel electrophoresis. However, the presence and level of the markers of the invention that are indicative of organ rejection can be determined by any techniques, including biochemical techniques, immunological techniques, and molecular biological techniques (detection of the presence of mRNA encoding a marker).

As exemplified herein, the level of the marker proteins can be evaluated by metabolic labeling of the proteins. As the metabolic labeling occurs during in vitro incubation of the tissue biopsy in the presence of culture medium supplemented with [$^{35}$S]-methionine, the level of each of the markers detected may be affected by the in vitro conditions. However, the data presented herein clearly demonstrate that these markers have diagnostic and prognostic significance. Thus, in a specific aspect, the present invention provides for detection of the marker or markers (whether by metabolic labeling or any of the other techniques disclosed herein) after in vitro culturing of the sample, e.g., by incubation for about 20 hours. In addition to metabolic (or biosynthetic) labeling with [$^{35}$S]-methionine, the invention further contemplates labeling with [$^{14}$C]-amino acids and [$^{3}$H]-amino acids (with the tritium substituted at non-labile positions).

Furthermore, it is fully expected that the increased level of expression of the markers of the invention in vitro correlates with increased levels of expression of the markers in vivo. Thus, while the levels of the markers detected after 20 hours of biosynthetic labeling does not necessarily reflect the actual levels of the markers in vivo, the invention contemplates that the levels of such markers will be elevated above the levels found in normal organs or organs at stage 0 of rejection. Accordingly, the invention provides for detection of the markers in samples obtained from a subject without further in vitro culturing. Thus, a biological sample can be directly analyzed after labeling of the proteins therein, e.g., by colorimetric staining using silver, gold, coomassie blue, or amido-schwartz, to mention a few techniques; isotopic labeling, e.g., with [$^{32}$P]-orthophosphate, [$^{125}$I], [$^{131}$I]; fluorescent or chemiluminescent tags; and immunological detection with labeled antibody or specific binding partner of a marker.

As the invention provides for detection of increased levels of expression of a marker or markers indicative of organ rejection, a corresponding method is to detect increased levels of expression of mRNA (or mRNAs) encoding a marker (or markers). Detection of mRNA can be accomplished by many techniques, including Northern analysis, reverse-transcriptase PCR (RT-PCR), in vitro expression, and comparable means for detecting the presence of RNA encoding a marker of the invention (see Sambrook et al., supra; *Current Protocols in Molecular Biology*, supra).

If a transplant patient develops antibodies to one or more of the marker proteins comprised by the invention, it will probably occur some time after the expression of the marker proteins during the first rejection episode (see, e.g., Auchincloss and Sachs, 1993, "Transplantation Graft Rejection," in *Fundamental Immunology, Third Edition*, William E. Paul editor, Raven Press: New York, pp. 1099–1141, 1129). However, thereafter the auto-immune response will occur immediately when the marker proteins are expressed and thus could be exploited diagnostically for the prediction of subsequent rejection episodes. The presence of increased levels of autoantibodies specific for the markers may indirectly indicate increased levels of expression of the markers, just as the presence and level of antibodies to an infectious agent indirectly indicate the presence of the agent. Thus, detection and measurement of autoantibodies to one or more markers of the invention are contemplated as indicative of increased levels of expression of the marker.

In a specific embodiment, at least some of the marker proteins comprised by the invention can be identified in human cell lines. Such cell lines may be cultivated to produce large amounts of cellular protein, which is then analyzed by 2D gel analysis as described herein. The spots on the gels are transferred to a polyvinyldifluoride (PVDF) or nitrocellulose membrane by Western blot technique to form a "marker map", and this is subsequently tested with serum from a patient. If the patient has synthesized autoantibodies to the respective marker proteins, these antibodies will bind to their respective antigen and may then be detected using, e.g., chromogenous or chemiluminescent techniques or radioactively labelled antibodies to human antibodies.

As noted above, the markers of the invention provide a diagnostic tool for predicting or differentially diagnosing organ rejection. In a further embodiment, quantitation of the level of one or more of the markers, and more preferably, comparison of the relative levels of two or more markers to each other, provides a sensitive and accurate means for diagnosing the stage of rejection. For example, as demonstrated in Example 1, infra, the level of IEF 1 present in a biopsy after 20 hours incubation in vitro increases by greater than 2-fold in stage 1A rejection, greater than 7-fold in a stage 2A rejection, etc. Thus, the relative level of IEF 1 is a diagnostic indicator of the stage of rejection.

Similarly, in a stage 1A rejection, the relative levels of IEF 1 an IEF 2 are equal; by stage 3A "to be," however, the relative level of IEF 1 is about double the relative level of IEF 2. Thus, comparison of the relative level of IEF 1 to IEF 2 provides an indicator of the stage of rejection.

Various such relationships of the relative levels of markers of the invention taken independently or by comparison with other markers greatly increase the accuracy and sensitivity of the diagnostic and prognostic methods of the invention. These relationships can be determined by examination of Table 2, infra, which relates to the levels of the markers as determined by a biosynthetic labeling assay. Other relationships can be readily determined by those of ordinary skill in the art using other techniques for detecting the markers, such as but not limited to molecular biological and immunological techniques, and correlating the observed levels of the markers with rejection stage. The stage of rejection can be determined by tissue biopsy as described in Billingham et al. (1990, J. Heart Transplant. 9:587–593) or a corresponding technique for rejection of organs other than the heart, or by correlating with the biosynthetic labeling technique as described above.

The present invention advantageously provides convenient kits for use by practitioners in the art for conveniently diagnosing the likelihood of onset or stage of organ rejection. Accordingly a test kit may be prepared for the demonstration of the presence and level of a marker of organ rejection. Generally, such a kit will comprise means for detecting the presence of a marker indicative of organ rejection in a biological sample from a subject, and means for determining whether the marker is present at an increased level relative to the level present in a corresponding biological sample from a normal subject or from the subject under observation prior to initiation of organ rejection phenomena, in appropriate containers, and optimally packaged with directions for use of the kit. In one particular aspect, the means for detecting the presence of the marker and for determining whether the marker is present at an increased level comprise a specific binding partner of the marker, such as an antibody, and means for detecting the level of binding of the specific binding partner of the marker to the marker. In another embodiment, in a kit of the invention, a label for proteins expressed by cells present in the biological sample is provided, as are means for detecting the level of labeling of the marker, and correspondingly, the level of the marker. In still another embodiment, the test kit comprises an oligonucleotide probe for mRNA encoding a marker expressed by cells present in the biological sample; and means for detecting the level of binding of the probe to the mRNA; wherein detection of and increased level of expression of the mRNA encoding the marker is indicative of an increased level of the marker.

In a preferred aspect, the test kit of the invention comprises means for detecting the presence of more than one marker indicative of organ rejection in a biological sample from a subject; and means for determining whether each marker is present at an increased level relative to the level present in a corresponding biological sample from a normal subject or at a subject prior to initiation of organ rejection phenomena.

In still a further example, a kit of the invention provides a known amount of the marker to be detected, in which the marker provided in the kit is labeled.

For example, a kit of the invention can provide in an appropriate container or containers:
  (a) a predetermined amount of at least one labeled immunochemically reactive component obtained by the direct or indirect attachment of a marker or a specific binding partner thereto, to a detectable label;
  (b) if necessary, other reagents; and
  (c) directions for use of said kit.
More specifically, the diagnostic test kit may comprise:
  (a) a known amount of the marker as described above (or a binding partner) generally bound to a solid phase to form an immunosorbent, or in the alternative, bound to a suitable tag, or plural such end products, etc. (or their binding partners) one of each;
  (b) if necessary, other reagents; and
  (c) directions for use of said test kit.

Therapeutic Implications of the Markers

The present invention contemplates that synthesis of rejection markers plays a modulatory role in organ rejection phenomena. Some or all of the rejection markers may be protective proteins, that either protect the organ from stress or immune activation. Alternatively, expression of other of the markers may have detrimental consequences, for example, if their synthesis could trigger immune destruction of the tissue.

Accordingly, the present invention provides for regulation of the expression of the markers in order to modulate rejection episodes. In one embodiment, a marker or markers are introduced into the cells in the organ subject to rejection (e.g., a donor organ for transplantation, or an organ suffering from autoimmune insult) under control of a constitutive promoter to buffer or protect the organ from rejection. In a particular embodiment, transgenic animals used to provide xenografts are prepared to express one or more of the markers at a level that is protective against organ rejection.

In one embodiment, a gene encoding a marker is introduced in vivo via a viral vector. Such vectors include an attenuated or defective DNA virus, such as but not limited to herpes simplex virus (HSV), human papillomavirus (HPV), Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a particular locus, e.g., the organ implicated in the rejection episode, can be specifically targeted with the vector. Examples of particular vectors include, but are not limited to, a defective herpes virus 1 (HSV1) vector (Kaplitt et al., 1991, Molec. Cell. Neurosci. 2:320–330), an attenuated adenovirus vector, such as the vector described by Stratford-Perricaudet et al. (1992, J. Clin. Invest. 90:626–630), and a defective adeno-associated virus vector (Samulski et al., 1987, J. Virol. 61:3096–3101; Samulski et al., 1989, J. Virol. 63:3822–3828).

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Feigner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as heart, pancreas, liver, kidney, and the brain. Lipids may be chemically coupled to other molecules for the purpose of targeting (see Mackey, et. al., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors are introduced into the desired host cells by methods known in the art, e.g., transfection, electroporation, microinjection, transduction, cell fusion, DEAE dextran, calcium phosphate precipitation, lipofection (liposome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

The present invention extends to the preparation of antisense nucleotides and ribozymes that may be used to interfere with the expression of the marker proteins at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA or DNA molecule (See Weintraub, 1990; Marcus-Sekura, 1988, Anal. Biochem. 172:298–95). Often the complementary RNA or DNA molecules will be synthesized using base analogs to improve the effectivity of the molecules, e.g., through increased stability against breakdown, increased binding strength to DNA or RNA, or increased permeability into cells. In the cell, they hybridize to complementary mRNA, forming a double stranded molecule, or to complementary DNA, forming a triple stranded molecule. The cell does not translate an mRNA in this double-stranded form, or efficiently transcribe such blocked DNA sequences. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. In addition, the tertiary structure of the mRNA plays an important role, and molecules that hybridize to non-self hybridized regions of the mRNA (for example the open "leaf" regions of snap-back or clover leaf structures, or regions between such regions of tertiary structure), are also particularly efficient at inhibiting translation. Antisense methods have been used to inhibit the expression of many genes in vitro (Marcus-Sekura, supra; Hambor et al., 1988, J. Exp. Med. 168:1237–45).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988, J. Am. Med. Assoc. 260:3030–4). Because they are sequence-specific, only mRNAs with particular sequences are inactivated.

Investigators have identified two types of ribozymes, Tetrahymena-type and "hammerhead"-type (Hassellhoff and Gerlach, 1988). Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences encoding marker proteins described and enabled herein may thus be used to prepare antisense molecules complementary to, and ribozymes that cleave, mRNAs for marker proteins, thus inhibiting expression of the gene encoding the marker, which may reduce the level of immune stimulation associated with organ rejection.

The intention further contemplates administration of a drug or drugs that modulate expression of a marker protein or proteins. The antibodies of the invention can be used to target such drugs to the desired location, i.e., the organ implicated in a rejection episode, by virtue of specific binding to the markers located in the organ cells. Coupling of a drug to an antibody can be by direct covalent conjugation or indirect association. Alternatively, a drug that modulates expression of a marker protein or proteins can be administered in a liposome, preferably a liposome that has been targeted to the organ involved, e.g., by association of an antibody therewith.

The present invention will be better understood by reference to the following Examples, which are provided by way of exemplification and not limitation.

EXAMPLE 1

IDENTIFICATION OF MARKERS OF ORGAN REJECTION

In this example, specific proteinaceous markers indicating rejection in endomyocardial biopsies following human heart transplantation are identified. The identified proteins are synthesized in very large amounts relative to their expression in normal or non-rejecting tissue for a certain number of weeks—dependent on the particular protein—before the actual rejection takes place. Such over-expression of several of the identified proteins is detectable at least 3–4 weeks prior to acute rejection. As early as one week after cessation of mild to severe rejection these proteins are no longer over-expressed. Compared to the commonly used histopathological method (HE-staining of biopsy sections) to evaluate rejection, the protein markers identified according to the present invention offer the potential of a correspondingly earlier prediction of the rejection course. These findings provide a new basis for understanding the rejection process, and not least will enable an earlier detection of rejection in heart transplant recipients. Accordingly, immunosuppressive treatment to avoid rejection and associated organ damage may be intensified at an earlier stage.

Human heart biopsies measuring approximately 0.25 mm$^3$ were collected by right heart catheterization, washed in Hank's buffer and placed into 100 μl of labeling medium [DMEM without methionine, containing 10% dialysed human AB serum and 1 mCi/ml [$^{35}$S]-methionine (Amersham SJ204)], and incubated for 20 h at 37° C. in a 5% $CO_2$/95% air humidified atmosphere. The biopsies were homogenized on ice in microhomogenizers using 100 μl of RNAse/DNAse buffer containing 25 μg/ml RNAse A (Cooper, Catalog No. LSO5650), 25 μg/ml DNAse I (Cooper, Catalog No. LSO6330), 30 mM NaCl, 5 mM $CaCl_2$, 5 mM $MgCl_2$, 20 mM Tris. HCl pH 8.5, and left to digest for 30 min at 4° C. They were then snap frozen in liquid nitrogen and freeze dried before solubilization in loading buffer [9.5 M urea, 2% w/v NONIDET-P40® (NP-40), 2% w/v AMPHOLOINES® pH range 7–9 (Pharmacia), 5% w/v 2-mercaptoethanol]. Polyacrylamide gels (3.5%, 185×1.55 mm, 8M urea, 2% NP-40) were prepared containing: for the IEF gels 6% AMPHOLINES® pH range 3.5–10, 2% AMPHOLINES® 5–7, and 2% SERVALYTES® 5–7 (Serva); and for the NEPHGE gels 3.3% AMPHOLINES® 7–9, 3.3% AMPHOLINES® 8–9.5, and 0.5% AMPHOLINES® 3.5–10. In each case, the actual mixture of ampholytes was calibrated for each batch. Phosphoric acid ($H_3PO_4$; 10 mM) was used as the anode buffer and degassed NaOH (20 mM) was used as the cathode buffer. IEF gels were prefocused at 1200 V, 133 μA (limiting values) per tube until the limiting voltage was reached. Half a million TCA precipitable counts were applied to both the IEF and NEPHGE gels and samples were overlayed with 8 M urea, 0.8% AMPHOLINES® (pH 5–7), and 0.2% AMPHOLINES® (pH 3.5–10). Electrophoresis was carried out at 1200 V, 133 μA (limiting) per gel: for 18 h for IEF gels; and for 4 h after the gels reached the limiting voltage for the NEPHGE gels. The gels were then extruded using compressed air and equilibrated for 6 min. before being frozen at −70° C.

When ready for further analysis, the gels were quickly thawed in a water bath (80° C.), incubated for 2 min. at room temperature, loaded and run on 12.5% polyacrylamide gels (200×200 mm, 1 mm) at 20° C. The second dimension gels were fixed for 45 min. In 45% methanol, 7.5% acetic acid, treated for 45 min. with AMPLIFY® (Amersham) to enhance fluorographic detection, dried, and exposed to x-ray film (AGFA Curix RP2) at −70° C. for 5 days. The developed images were compared either visually or with an image processing computer (BioImage program version 4.5 M, Millipore).

All ampholines used in the foregoing experiments were obtained from Pharmacia, with the exception of the SERVALYTES® ampholines obtained from Serva.

Biopsies were collected within the first year after transplantation in accordance with the Helsinki declaration II as part of the routine follow up or when rejection was suspected. All patients were treated according to the same immunosuppressive protocol, including cyclosporin, azathioprine, and prednisolone on the basis of the results obtained by standard biochemical and histological criteria. None of the patients were treated for active infections at the time the biopsy was collected. From a total of thirty-six patients (9 women and 27 men ranging in age from 22 to 56 years), a total of 92 biopsies were biosynthetically labeled with [$^{35}$S]-methionine for 20 hours in vitro. Thereafter, the biopsies were analysed by 2-dimensional gel electrophoresis (IEF or NEPHGE).

Two examples of the resulting fluorograms from the rejection grade 0 and 3A are shown in FIG. 1A and 1B, respectively. Comparison of these patterns clearly illustrates, by differences in protein spot intensity, a number of very significant changes in protein expression: proteins that are expressed at non-detectable or low detectable levels in the grade 0 biopsy are greatly over expressed in the grade 3A biopsy (indicated by arrows and numbers in FIG. 1B). As such, they could be used as markers for acute rejection.

In order to evaluate putative variation in the expression of these markers, biopsies were taken from various parts of a rejected heart (grade 4) after its removal during a retransplantation operation. These biopsies showed that the marker proteins were highly expressed in the walls of the left and right ventricles, and at lower levels in both atria. The isoelectric point and molecular weight of the marker proteins, as determined by 2D gel analysis, are summarized in Table 1.

TABLE 1

Marker proteins.

| Protein | pI | MW |
|---|---|---|
| IEF 1A | 5.92 | 122,600 |
| IEF 1B | 5.83 | 123,100 |
| IEF 2A | 6.20 | 75,500 |
| IEF 2B | 6.15 | 76,100 |
| IEF 3 | 6.09 | 49,900 |
| IEF 4 | 6.86 | 42,700 |
| IEF 5A | 6.12 | 39,100 |
| IEF 5B | 6.08 | 39,200 |
| IEF 5C | 5.96 | 39,300 |
| IEF 6 | 5.07 | 21,800 |
| IEF 7 | 5.60 | 20,400 |
| IEF 8 | 5.72 | 16,400 |
| NEPHGE 1A | 7.92 | 78,900 |
| NEPHGE 1B | 7.87 | 79,000 |
| NEPHGE 1C | 7.83 | 79,200 |
| NEPHGE 1D | 7.76 | 79,200 |
| NEPHGE 2 | 7.73 | 53,700 |
| NEPHGE 3 | 7.91 | 53,100 |
| NEPHGE 4 | 9.96 | 48,300 |
| NEPHGE 5 | 8.01 | 44,900 |
| NEPHGE 6 | 7.84 | 42,900 |
| NEPHGE 7 | 9.38 | 38,800 |
| NEPHGE 8 | 6.90 | 36,600 |
| NEPHGE 9 | 6.89 | 20,500 |
| NEPHGE 10 | 8.09 | 10,000 |

Figure 2:
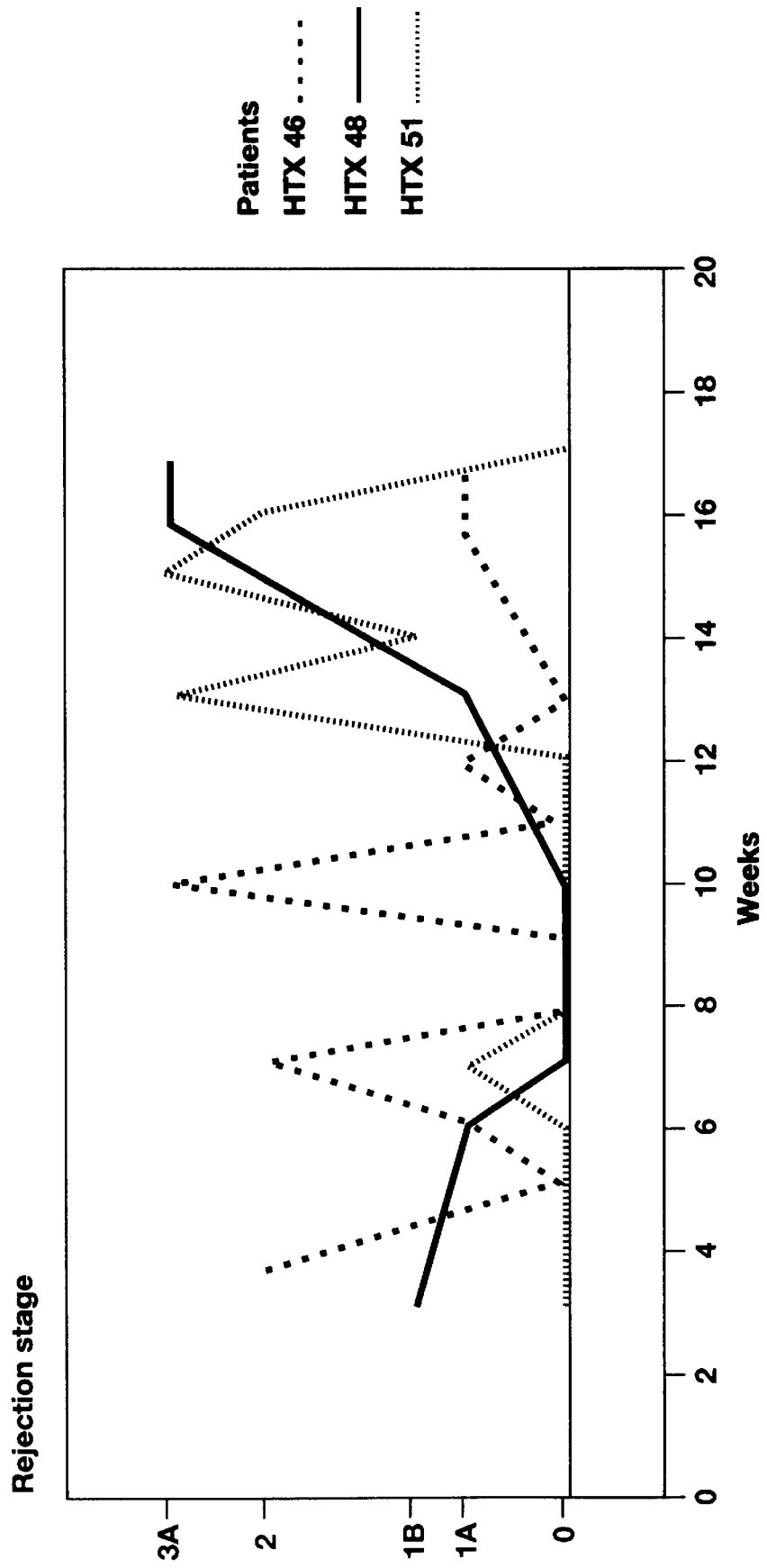
FIG. 2. Clinical course of three patients following heart transplantation. HTX no. is the patient identification number.

In the classical clinical picture following heart transplantation, the patient goes through phases of varying degrees of rejection as illustrated in FIG. 2. The graphs illustrate three examples of the exacerable course of rejection episodes evaluated by standard histological criteria. HTX no. is the patient identification number. The arrow indicates the time point when the biopsies were taken for the two dimensional gel analysis (set to time 0). Consecutive biopsies were collected in corresponding courses from other patients.

Patient HTX 51 had an exacerbated course and underwent a rapid change from rejection grade 0 to 3A. This patient responded to treatment, returning to grade 0. This event occurred within 2 weeks. Patient HTX 46 was in a more stable condition, but underwent periods of moderate (grade 3A) rejection. Patient HTX 40 only went through one period of moderate rejection throughout the observation period.

The marker proteins undergo modulation of expression during the course of a rejection episode as illustrated by differences in staining in two regions of the gels (around IEF 1 and IEF 6–8 in FIG. 1B). These regions are shown enlarged in FIGS. 3A–F and 3G–L.

Figure 3:
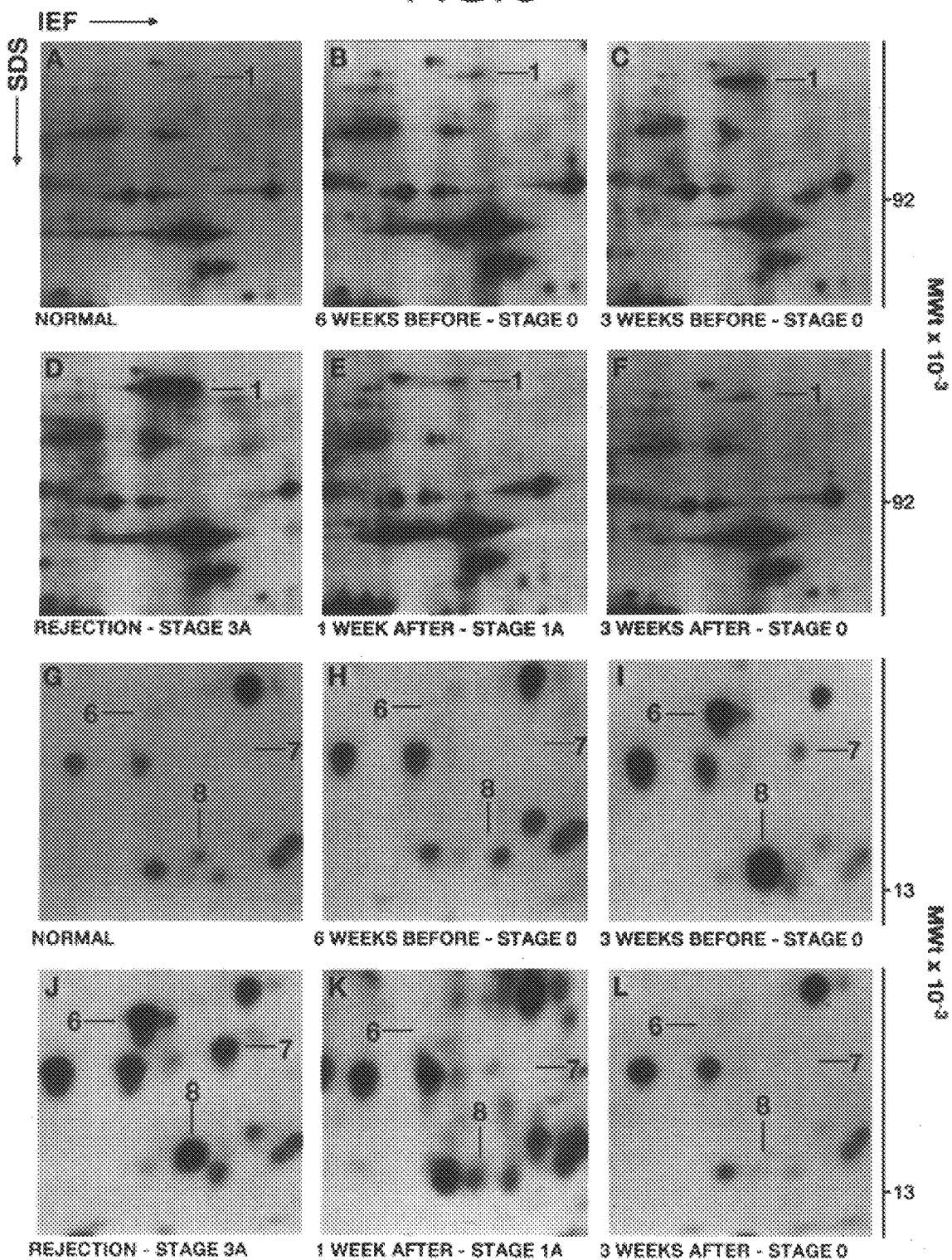
FIG. 3. Expression of the marker proteins at different stages of rejection. In (A) through (F) and (G) through (L) are two series of fluorograms from two different gel regions of the IEF gels. Biopsies were collected from a normal donor heart (A and G); and from heart transplanted patients 6 weeks before a moderate rejection (B and H; stage 0), 3 weeks before a moderate rejection (C and I; stage 0), at moderate rejection (D and J; stage 3A), one week after moderate rejection (E and K; stage 1A), and finally 3 weeks after moderate rejection (F and L; stage 0). Samples were processed and gels run as for FIG. 1.

Some of the marker proteins are expressed at low or non-detectable levels in non-transplanted biopsies (FIG. 3, A and G). In transplanted patients, these proteins are unchanged six weeks prior to moderate rejection (FIG. 3, B and H). Thereafter, a hierarchy of protein changes occur in the weeks leading up to a rejection episode. For instance, proteins, IEF 1, 6 and 8 were greatly increased by 3–4 weeks before rejection (FIG. 3, C and I), whereas IEF 7 is expressed at high levels only during rejection (FIG. 3, J). The marker proteins were always over-expressed in grade 3A biopsies from all five patients (FIG. 3, D and J). However, the expression of the marker proteins, while still elevated, was greatly reduced one week after the rejection episode, when the grade of the biopsy was 1A (FIG. 3, E and K), and had returned to normal levels two weeks after moderate rejection, when the biopsy was histologically graded 0 (FIG. 3, F and L). No increase was detected in the marker proteins prior to grade 1A rejection (not shown).

Visually, it was possible to detect 18 markers for moderate rejection. The level of expression of the markers can be analyzed by computerized image analysis, thus allowing quantitative analysis during the rejection episode. Quantitation of the films demonstrated that the marker proteins were over-expressed at levels ranging from about 3 to more than 120-fold (Table 2). The majority of the markers were expressed by a factor greater than ten-fold above normal levels in grade 0. Two of the markers (IEF 6 and NEPHGE 10) were over-expressed more than 100 times compared to level of expression in the grade 0 biopsy.

TABLE 2

Protein Expression Ratio

| | IEF | | | | | | | |
|---|---|---|---|---|---|---|---|---|
| | 1 | 2 | 3 | 4 | 5 | 6 | 7 | 8 |
| Donor | 0.6 | 0.7 | 1.2 | 1.2 | 1.8 | 1.1 | 3.3 | 4.2 |
| 0 | 1.0 | 1.0 | 1.0 | 1.0 | 1.0 | 1.0 | 1.0 | 1.0 |
| 1A | 2.4 | 2.2 | 1.1 | 0.7 | 1.1 | 0.1 | 0.7 | 0.1 |
| 2A | 7.2 | 1.5 | 0.8 | 0.6 | 1.0 | 0.5 | 0.3 | 1.4 |
| 3A to be | 13.8 | 4.4 | 8.7 | 1.4 | 8.1 | 75.8 | 28.0 | 133.9 |
| 3A | 41.0 | 5.3 | 10.6 | 2.8 | 13.9 | 106.0 | 72.3 | 84.1 |
| % IOD (0) | 0.043 | 0.020 | 0.111 | 0.034 | 0.061 | 0.008 | 0.003 | 0.009 |

| | NEPHGE | | | | | | | | | |
|---|---|---|---|---|---|---|---|---|---|---|
| | 1 | 2 | 3 | 4 | 5 | 6 | 7 | 8 | 9 | 10 |
| Donor | 1.1 | 0.5 | 1.3 | 1.8 | 0.2 | 0.3 | 1.0 | 0.4 | 2.0 | 0.3 |
| 0 | 1.0 | 1.0 | 1.0 | 1.0 | 1.0 | 1.0 | 1.0 | 1.0 | 1.0 | 1.0 |
| 1A | 1.5 | 0.8 | 1.5 | 0.9 | 0.1 | 2.0 | 1.0 | 0.4 | 0.5 | 1.0 |
| 2A | 0.1 | 0.6 | 0.1 | 0.6 | 0.3 | 1.6 | 0.5 | 0.4 | 6.0 | 0.6 |
| 3A to be | 2.5 | 1.0 | 1.5 | 3.2 | 2.8 | 9.9 | 7.5 | 2.3 | 0.8 | 21.6 |
| 3A | 17.6 | 4.8 | 6.2 | 22.7 | 19.1 | 51.1 | 14.5 | 22.9 | 9.5 | 119.9 |
| % IOD (0) | 0.008 | 0.020 | 00.057 | 0.010 | 0.010 | 0.008 | 0.002 | 0.018 | 0.004 | 0.016 |

The expression of the marker proteins was quantitated from the fluorograms of the 2D gels as integrated optical density (IOD) of the protein in relation to the total optical density from all the detected proteins. The first line of the table refers to the IEF of NEPHGE marker protein. The values given in the table are the ratio of expression of the marker proteins relative to the average expression of the same protein in a grade 0 biopsy. The percentage of the individual markerproteins relative to the total protein expression in a grade 0 biopsy is given in the bottom line. The protein expression ratios are given in groups according to the histological diagnosis of the endomyocardial biopsies. "Pre-3A" represents any biopsy collected up to 5 weeks before a grade 3A diagnosis. The histological and electrophoretic analyses were blinded, i.e., carried out independently and by different persons who were unaware of the results reached by the otheranalytical technique. The expression of the marker proteins was quantitated by scanning the fluorographs using a Truvel scanner (Millipore), and converted the images to 1024 × 1024 pixel, 8 bit images. These were imported into the BioImage program version 4.6M (Millipore) running on a Sun Sparc workstation. Spot boundaries were identified by the program and the sum of the grey levels for all pixels inside the boundary, minus a local background value for each pixel, gave a measureof the expression of the protein in question (integrated optical density, IOD). This was carried out for all spots detected and the expression of each protein was expressed as a percentage of the total of all the proteins detected (% IOD).

While the function of these marker proteins is not yet known, they could stem from either the activation of genes in cardiac tissue cells, e.g., myocytes, vascular cells, fibroblasts in the interstitium, or from infiltrating cells. These markers are not considered to stem from the activation of an infection because they are found in the donor tissue prior to implantation in very low, but definite amounts and thus appear to be normal cellular proteins of the heart (FIGS. 3A and G). Comparison of the biopsies taken before and after implantation (FIGS. 3A and B, 3G and H) demonstrate that the expression of the markers is identical and therefore their expression does not seem to be induced by the immunosuppressive treatment.

While none of the marker proteins appear to correspond to known proteins, they may represent proteins synthesized secondary to inflammatory mediators (Mose Larsen et al., 1994, Proc. Int. Soc. Heart Res.) or proteins regulating heart muscle contraction. For instance, the immunoglobulin-family cell surface protein VCAM-1, which is induced on inflamed endothelium by proinflammatory cytokines, has been shown to accumulate in venous capillaries and post capillary venules in endomyocardial biopsies using indirect immunofluorescence one week prior to histologically identifiable rejection (Ferran et al., 1993, Transplantation 55:605–609; Bevilacqua, 1993, Annu. Rev. Immunol. 11:767–804; Adams and Shaw, 1994, Lancet 343:831–836). ICAM-1 is a marker of immune activation and endothelial damage, but has not been found to be correlated with cellular rejection as assessed by endomyocardial biopsy (Ballantyne et al., 1994, J. Heart Lung Transplant. 13:597–603). Markers of myocardial damage such as creatine kinase MB and myoglobin have not been useful in identifying rejection in heart transplanted patients (Ladowski et al., 1992, Chest 102:1520–1; Jennison et al., 1992, Circulation Suppl 86:1–844; Gash et al., 1994, J. Heart Lung Transplant. 13:451–454).

As noted in the following Example, partial amino acid sequence information has been obtained from six proteins.

Over-expression of the 18 marker proteins has been identified in heart transplanted patients undergoing rejection episodes. Since several of the marker proteins are highly over-expressed at least four weeks prior to a rejection episode, they open possibilities to develop rapid prognostic tools for the early prediction of rejection. Furthermore, this observation holds promise for a new insiglht into the molecular basis of the rejection process following transplantation, in particular of the human heart.

EXAMPLE 2

DETERMINATION OF PARTIAL AMINO ACID SEQUENCES

A number of marker proteins identified on the IEF gels were analyzed further by microsequencing. The proteins were eletroeluted using a 0.1% SDS, 27.5 mM Tris-HCl, 95.9 mM glycine, pH 8.3 buffer and recovered on PVDF membrane. The membrane was washed and saturated with 0.2% polyvinylpyrrolidone. The membrane associated protein was then trypsin digested with 0.5 μg trypsin for 24 hrs at 37° C. in 100 μl of 100 mM Tris-HCl, pH 8.5, 10% acetonitrile. The peptides were separated by reverse phase-HPLC using a C-18 column with a trifluoroacetic acid-acetonitrile gradient. Peaks were detected at 214 nm and manually collected and treated with POLY-BRENE® (Applied Biosystems). Sequencing of the peptides was carried out in a pulsed-liquid phase sequencer (Applied Biosystems, model 477A) equipped with an on-line phenylthiohydantoin amino acid derivative analyzer (Applied Biosystems, model 120A). The information obtained is reported in Table 3.

TABLE 3

Partial Amino Acid Sequence Information

| IEF | SEQUENCE | (SEQ ID NO:) |
|---|---|---|
| 1 | M L P Q L I P L L R V A | (SEQ ID NO:1) |
| 1 | (G) G H G F E G E | (SEQ ID NO:2) |
| 1 | K V A L P X S P N G | (SEQ ID NO:3) |
| 3 | X I A K G X G A G Y P K G I X T E X F | (SEQ ID NO:4) |
| 3 | (R) X Q Y I V T A M | (SEQ ID NO:5) |
| 3 | (N) D Q E V Q P X A V | (SEQ ID NO:6) |
| 3 | X X N E V X X I T X | (SEQ ID NO:7) |
| 5 | A L X Q N P T Q A E V L R | (SEQ ID NO:8) |
| 6 | X Q G Q V (A) H G D/R X X A P Y | (SEQ ID NO:9) |
| 6 | I V I Q V X L X N E M T G M | (SEQ ID NO:10) |
| 6 | X X M T N T V I X X | (SEQ ID NO:11) |
| 7 | A V Q E L E K | (SEQ ID NO:12) |
| 7 | I L A E R | (SEQ ID NO:13) |
| 7 | X E F V X V T K | (SEQ ID NO:14) |
| 7 | X X E E A V L V S L (N) | (SEQ ID NO:15) |
| 8 | M T K A E I F K G P K V L E Q V X F X | (SEQ ID NO:16) |

After the partial sequence information was obtained, the sequences were searched for homology or similarity to known proteins. The program GCG (Genetics Computer Group, Wisconsin) was used to search the SWISS-PROT protein sequence database (40,292 sequences, 14,147,368 symbols) with the FASTA subroutine, and using the EMBL-genebank (257,716 sequences, 263,275,079 symbols) using the subroutine tFASTA so that the amino acid sequences were translated to base sequences and these were used to search all entered sequences using a word size of 2.

The first partial sequence for protein IEF 1 (SEQ ID NO: 1) showed low similarity (60% match) with a human atrial natriuretic peptide receptor A precursor (ID ANPA). A second partial sequence from this spot (SEQ ID NO:2) demonstrated moderate homology or similarity with human cytokeratin 9 (75% match, ID K1CI). A third partial sequence (SEQ ID NO:3) had only a 62.5% match with a human Von Willebrand factor precursor (ID VWF_HUMAN), and it has similarity (about 60% match) with the carboxypeptidase H precursor of many species (rabbit, bovine, human, rat, and mouse). Thus, IEF 1 appears to be a novel protein, i.e., a protein that has not been sequenced previously.

One partial amino acid sequence of IEF 3 (SEQ ID NO:5) showed significant homology to a spore germination protein (GRC1_BACSU, 77.8% match over 9 amino acid residues). It also had some similarity or homology (57.1% match) to rat and human insulin responsive glucose transporter type 4 (ID GTR4_RAT and GTR4_HUMAN). A second partial sequence from this protein (SEQ ID NO:6), however, manifested no similarity with these proteins, but was somewhat similar to both human transcription factor 7 and angiotensin converting enzyme precursor (both having 80.0% matches). Still a third partial sequence (SEQ ID NO:7) had less than 60% match with any database proteins. Thus, IEF 3 appears to be a novel protein.

Partial amino acid sequence data for IEF 5 (SEQ ID NO:8) shows 92.3% homology with a 13 amino acid overlap to human and rat slow-twitch muscle (ventricular isoform) of myosin light chain (MLC) 1 (IDs MLEV_HUMAN and MLEV_RAT, respectively), and high degree of similarity to other forms of the myosin light chains, including atrial and foetal, from several species including mouse, rat, human, and chicken. However, the observed molecular weight of IEF 5 (39,100 to 39,300 Daltons) is much larger than that of myosin light chain (about 22 kilo-Daltons). Myosin light chain is not known to have a pro-form. Thus, it appears that IEF 5 represents a novel protein having a region of homology or similarity with myosin light chain.

Marker IEF 6 yielded a partial amino acid sequence (SEQ ID NO:9) with no known homology or similarity to proteins in the database. A second partial sequence (SEQ ID NO: 10) 4% had very low similarity (45% match) in an 11 amino acid overlap with the CD81 antigen, a 26 kilo-Dalton cell surface protein TAPA-1. A third internal sequence of IEF 6 (SEQ ID NO:11) was very similar to a number of diverse proteins, including human complement C3 precursor (ID CO3_HUMAN, 83.3% match), or the upstream stimulatory factor 1 (ID USF1_HUMAN). However, none of the proteins that shared partial sequence similarity were of comparable size to IEF 6. Thus, IEF 6 appears to be a novel protein.

Marker IEF 7 yielded four internal sequences, three of which were searched on the database. SEQ ID NO: 12 was similar to with human myosin heavy chain (greater than 90% match), both the cellular non-muscle heavy chain type A (ID MYSN_HUMAN) and the smooth muscle isoform (ID MYST_HUMAN). There was also a weaker homology or similarity (71.4% match) to the human endothelial nitric oxide synthase (ID NOS3_HUMAN). However, a second internal sequence (SEQ ID NO:13) showed no similarity to myosin heavy chain. This partial sequence was highly similar (100% match) to a commonly observed 5 amino acid motif with identity in many species and identified human proteins, including: choline kinase (ID KICH_HUMAN) and myo-inositol-1 (or -4)-monophosphate (ID MYOP_HUMAN). This sequence ALSO had a 94.2% match with human troponin T (slow skeletal and cardiac forms; ID TRT_HUMAN), and greater than 90% matches with troponin Ts from a number of other species. The third internal sequence (SEQ ID NO:15) was less similar to any known protein, with the greatest similarity to a hypothetical *E. Coli* protein. However, this partial sequence was greater than 65% matched with troponin T isoforms from a number of species, with 66.7% match with human slow skeletal troponin T. Thus, while on balance IEF 7 shares some sequence similarity with troponin T, it too appears to be a novel protein.

The single internal sequence from IEF 8 (SEQ ID NO:16) had a 62.5% match with rabbit cardiac calsequestrin precursor (ID CAQC_RABBIT).

More detailed analysis of these partial amino acid sequences using the tFASTA search routine of the GCG revealed additional similarities to a number of proteins or unknown open reading frames. However, in the cases where more than one peptide fragment has been sequenced from the same protein, even this much more extensive search was not able to identify a unique protein to any of the markers described in this Example. Thus, we conclude that these are proteins that have not previously been isolated in an amount sufficient for sequencing.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

Various references are cited throughout this specification, each of which is incorporated herein by reference in its entirety.

What is claimed is:

1. A method for evaluating the likelihood of organ rejection comprising detecting the presence of an amount of at least one marker indicative of organ rejection in a biological sample from a subject suspected of being in danger of organ rejection, wherein the at least one marker is a protein expressed by the cells in the organ suspected of being rejected, and wherein detection of the presence of an amount of the at least one marker is indicative of an increased likelihood of or the onset of organ rejection, wherein the at least one marker is selected from the group consisting of:

| Marker Protein | pI | MW |
| --- | --- | --- |
| IEF 1A | 5.92 | 122,600; |
| IEF 1B | 5.83 | 123,100; |
| IEF 2A | 6.20 | 75,500; |
| IEF 2B | 6.15 | 76,100; |
| IEF 3 | 6.09 | 49,900; |
| IEF 4 | 6.86 | 42,700; |
| IEF 5A | 6.12 | 39,100; |
| IEF 5B | 6.08 | 39,200; |
| IEF 5C | 5.95 | 20,400; |
| IEF 6 | 5.07 | 21,800; |
| IEF 7 | 5.60 | 20,400; |
| IEF 8 | 5.72 | 16,400; |
| NEPHGE 1A | 7.92 | 78,900; |
| NEPHGE 1B | 7.87 | 79,000; |
| NEPHGE 1C | 7.83 | 79,200; |
| NEPHGE 1D | 7.76 | 79,200; |
| NEPHE 2 | 7.73 | 53,700; |
| NEPHGE 3 | 7.91 | 53,100; |
| NEPHGE 4 | 9.96 | 48,300; |
| NEPHGE 5 | 8.01 | 44,900; |
| NEPHGE 6 | 7.84 | 42,900; |
| NEPHGE 7 | 9.38 | 38,800; |
| NEPHGE 8 | 6.90 | 36,600; |
| NEPHGE 9 | 6.89 | 20,500; and |
| NEPHGE 10 | 8.09 | 10,000, | wherein pI is the isoelectric point of the at least one marker as determined by isoelectric focusing for acidic or neutral proteins and by non-equilibrium pH gradient gel electrophoresis for basic or neutral proteins, and molecular weight of the at least one marker is determined on a polyacrylamide gel.

2. The method according to claim 1 wherein the organ is a heart.

3. The method according to claim 2 wherein the heart is a heart that has been transplanted into the subject.

4. The method according to claim 3 wherein the markers IEF 1, IEF 3, IEF 5, IEF 6, IEF 7, and IEF 8 have the following partial amino acid sequences:
   IEF 1: M L P Q L I P L L R V A (SEQ ID NO:1), (G) G H G F E G E (SEQ ID NO:2), and K V A L P X S P N G (SEQ ID NO:3);
   IEF 3: X I A K G X G A G Y P K G I X T E X F (SEQ ID NO:4), (R) X Q Y I V T A M (SEQ ID NO:5), (N) D Q E V Q P X A V (SEQ ID NO:6), and X X N E V X X I T X (SEQ ID NO:7);
   IEF 5: A L X Q N P T Q A E V L R (SEQ ID NO:8);
   IEF 6: X Q C Q V (A) H G D/R X X A P Y (SEQ ID NO:9), I V I Q V X L X N E M T G M (SEQ ID NO:10), and X X M T N T V I X X (SEQ ID NO:11);
   IEF 7: A V Q E L E K (SEQ ID NO:12), I L A E R(SEQ ID NO:13), X E F V X V T K (SEQ ID NO:14), and X X E E A V L V S L (N)(SEQ ID NO:15); and
   IEF8: M T F K A E I F K G P K V L E Q V X F X (SEQ ID NO:16).

5. The metilod according to claim 1 wherein the markers are selected from the group consisting of IEF 1A, IEF 1B, IEF 6, IEF 7, IEF 8, NEPHGE 1A, NEPHGE 1B, NEPHGE 1C, NEPHGE 1D, NEPHGE 6, NEPHGE 9, and NEPHGE 10.

6. The method according to claim 1 wherein the presence of an amount of a marker indicative of organ rejection is detected by biochemical analysis.

7. The method according to claim 6 wherein the biochemical analysis is two-dimensional gel electrophoresis.

8. The method according to claim 1 wherein the presence of an amount of a marker indicative of organ rejection is detected by immunological analysis.

9. The method according to claim 8 wherein the immunological analysis is selected from the group consisting of immunoblotting, enzyme-linked immunosorbent assay (ELISA), radio-immunoassay (RIA), agglutination, immunofluorescence, immunochemiluminescence, immunochromatography, biosensor, optical sensor, and immunoprecipitation.

10. The method according to claim 1 wherein the biological sample is a sample selected from the group consisting of blood, serum, plasma, tissue biopsy, organ biopsy, synovial fluid, urine, bile fluid, cerebrospinal fluid, saliva, mucosal secretion, effusion, and sweat.

11. The method according to any of claims 1–10 comprising detecting the presence of an amount of more than one marker indicative of organ rejection in a biological sample from a subject suspected of being in danger of organ rejection, wherein each marker is a protein expressed by the cells in the organ suspected of being rejected, and wherein the detection of the presence of an amount of more than one of the markers is indicative of an increased likelihood of or the onset of organ rejection.

12. A test kit for evaluating the likelihood of organ rejection, comprising:
a) a predetermined amount of at least one labeled component obtained by the direct or indirect attachment of at least one marker or a specific binding partner thereto, to a detectable label, wherein the at least one marker is selected from the group consisting of:

| Marker Protein | pI | MW |
| --- | --- | --- |
| IEF 1A | 5.92 | 122,600; |
| IEF 1B | 5.83 | 123,100; |
| IEF 2A | 6.20 | 75,500; |
| IEF 2B | 6.15 | 76,100; |
| IEF 3 | 6.09 | 49,900; |
| IEF 4 | 6.86 | 42,700; |
| IEF 5A | 6.12 | 39,100; |
| IEF 5B | 6.08 | 39,200; |
| IEF 5C | 5.96 | 20,400; |
| IEF 6 | 5.07 | 21,800; |
| IEF 7 | 5.60 | 20,400; |
| IEF 8 | 5.72 | 16,400; |
| NEPHGE 1A | 7.92 | 78,900; |
| NEPHGE 1B | 7.87 | 79,000; |
| NEPHGE 1C | 7.83 | 79,200; |
| NEPHGE 1D | 7.76 | 79,200; |
| NEPHE 2 | 7.73 | 53,700; |
| NEPHGE 3 | 7.91 | 53,100; |
| NEPHGE 4 | 9.96 | 48,300; |
| NEPHGE 5 | 8.01 | 44,900; |
| NEPHGE 6 | 7.84 | 42,900; |
| NEPHGE 7 | 9.38 | 38,800; |
| NEPHGE 8 | 6.90 | 36,600; |
| NEPHGE 9 | 6.89 | 20,500; and |
| NEPHGE 10 | 8.09 | 10,000, | wherein pI is the isoelectric point of the at least one marker as determined by isoelectric focusing for acidic or neutral proteins and by non-equilibrium pH gradient gel electrophoresis for basic or neutral proteins, and molecular weight of the at least one marker is determined on a polyacrylamide gel; and b) directions for using said kit.

13. The test kit of claim 12 wherein the specific binding partner of the at least one marker is an antibody.

14. The test kit of claim 12 wherein the detectable label is selected from the group consisting of silver stain, Coomasie Blue stain, amido-schwartz, radio labels, metallic sol particles, dye sol particles, dyed latex, dyes encapsulated in liposomes, fluorescent moieties, luminescent moieties, enzymes and biosynthetic labeling.

15. A marker indicative of organ rejection in a biological sample from a subject experiencing an organ rejection, wherein the marker is a protein expressed by the cells in the organ suspected of being rejected, and said marker is selected from the group consisting of:

| Marker Protein | pI | MW |
| --- | --- | --- |
| IEF 1A | 5.92 | 122,600; |
| IEF 1B | 5.83 | 123,100; |
| IEF 2A | 6.20 | 75,500; |
| IEF 2B | 6.15 | 76,100; |
| IEF 3 | 6.09 | 49,900; |
| IEF 4 | 6.86 | 42,700; |
| IEF 5A | 6.12 | 39,100; |
| IEF 5B | 6.08 | 39,200; |
| IEF 5C | 5.96 | 20,400; |
| IEF 6 | 5.07 | 21,800; |
| IEF 7 | 5.60 | 20,400; |
| IEF 8 | 5.72 | 16,400; |
| NEPHGE 1A | 7.92 | 78,900; |
| NEPHGE 1B | 7.87 | 79,000; |
| NEPHGE 1C | 7.83 | 79,200; |
| NEPHGE 1D | 7.76 | 79,200; |
| NEPHE 2 | 7.73 | 53,700; |
| NEPHGE 3 | 7.91 | 53,100; |
| NEPHGE 4 | 9.96 | 48,300; |
| NEPHGE 5 | 8.01 | 44,900; |
| NEPHGE 6 | 7.84 | 42,900; |
| NEPHGE 7 | 9.38 | 38,800; |
| NEPHGE 8 | 6.90 | 36,600; |
| NEPHGE 9 | 6.89 | 20,500; and |
| NEPHGE 10 | 8.09 | 10,000, | wherein pI is the isoelectric point of the marker as determined by isoelectric focusing for acidic or neutral proteins and by non-equilibrium pH gradient gel electrophoresis for basic or neutral proteins, and molecular weight is determined on a polyacrylamide gel.

16. The marker of claim 15, wherein the markers IEF 1, IEF 3, IEF 5, IEF 6, IEF 7, and IEF 8 have the following partial amino acid sequences:

IEF 1: M L P Q L I P L L R V A (SEQ ID NO:1), (G) G H G F E G E (SEQ ID NO:2), and K V A L P X S P N G (SEQ ID NO:3);

IEF 3: X I A K G X G A G Y P K G I X T E X F (SEQ ID NO:4), (R) X Q Y I V T A M (SEQ ID NO:5), (N) D Q E V Q P X A V (SEQ ID NO:6), and X X N E V X X I T X (SEQ ID NO:7);

IEF 5: A L X Q N P T Q A E V L R (SEQ ID NO:8);

IEF 6: X Q G Q V (A) H G D/R X X A P Y (SEQ ID NO:9), I V I Q V X L X N E M T G M (SEQ ID NO:10), and X X M T N T V I X X (SEQ ID NO:11);

IEF 7: A V Q E L E K (SEQ ID NO: 12), I L A E R(SEQ ID NO:13), X E F V X V T K (SEQ ID NO: 14), and X X E E A V L V S L (N)(SEQ ID NO:15); and

IEF 8: M T F K A E I F K G P K V L E Q V X F X (SEQ ID NO: 16).

* * * * *